United States Patent
Chen et al.

(10) Patent No.: US 7,113,623 B2
(45) Date of Patent: Sep. 26, 2006

(54) METHODS AND SYSTEMS FOR DISPLAY AND ANALYSIS OF MOVING ARTERIAL TREE STRUCTURES

(75) Inventors: Shiuh-Yung James Chen, Englewood, CO (US); John D. Carroll, Littleton, CO (US)

(73) Assignee: The Regents of the University of Colorado, Boulder, CO (US)

( * ) Notice: Subject to any disclaimer, the term of this patent is extended or adjusted under 35 U.S.C. 154(b) by 642 days.

(21) Appl. No.: 10/267,151

(22) Filed: Oct. 8, 2002

(65) Prior Publication Data

US 2004/0066958 A1 Apr. 8, 2004

(51) Int. Cl.
*G06K 9/00* (2006.01)
*G06T 15/00* (2006.01)
*G09G 5/02* (2006.01)
*A61B 5/02* (2006.01)

(52) U.S. Cl. .................. 382/128; 382/154; 345/419; 345/589; 600/500; 600/508

(58) Field of Classification Search ........ 382/128–132, 382/154; 345/419, 589; 600/481, 500, 508
See application file for complete search history.

(56) References Cited

U.S. PATENT DOCUMENTS

| | | | |
|---|---|---|---|
| 4,839,822 A | | 6/1989 | Dormond et al. |
| 4,875,165 A | | 10/1989 | Fencil et al. |
| 4,878,115 A | | 10/1989 | Elion |
| 5,151,856 A | * | 9/1992 | Halmann et al. ........... 600/508 |
| 5,709,206 A | | 1/1998 | Teboul et al. |
| 5,839,440 A | | 11/1998 | Liou et al. |
| 6,047,080 A | * | 4/2000 | Chen et al. ................. 382/128 |
| 6,115,485 A | * | 9/2000 | Dumoulin et al. .......... 382/128 |
| 6,366,800 B1 | * | 4/2002 | Vining et al. .............. 600/425 |
| 6,501,848 B1 | * | 12/2002 | Carroll et al. .............. 382/128 |
| 6,546,271 B1 | * | 4/2003 | Reisfeld ..................... 600/407 |

(Continued)

FOREIGN PATENT DOCUMENTS

EP 1210910 A1 6/2002

OTHER PUBLICATIONS

Chen and Metz, Improved Determination of Biplane Imaging Geometry from Two Projection Images and its Application to Three-dimensional Reconstruction of Coronary Arterial Trees. Medical Physics, May 1997, vol. 24, No. 5, pp. 633-654.

(Continued)

*Primary Examiner*—Bhavesh M. Mehta
*Assistant Examiner*—Anthony Mackowey
(74) *Attorney, Agent, or Firm*—Duft Bornsen & Fishman; Daniel Fishman

(57) ABSTRACT

Methods and systems for reconstruction of a three-dimensional representation of a moving arterial tree structure from a pair of sequences of time varying two-dimensional images thereof and for analysis of the reconstructed representation. In one aspect of the invention, a pair of time varying arteriographic image sequences are used to reconstruct a three-dimensional representation of the vascular tree structure as it moves through a cardiac cycle. The arteriographic image sequences maybe obtained from a biplane imaging system or from two sequences of images using a single plane imaging system. Another aspect of the invention then applies analysis methods and systems utilizing the three-dimensional representation to analyze various kinematic and deformation measures of the moving vascular structure. Analysis results may be presented to the user using color coded indicia to identify various kinematic and deformation measures of the vascular tree.

34 Claims, 26 Drawing Sheets

U.S. PATENT DOCUMENTS

| | | | |
|---|---|---|---|
| 6,647,135 B1 * | 11/2003 | Bonnefous | 382/128 |
| 6,718,054 B1 * | 4/2004 | Lorigo et al. | 382/128 |
| 2001/0031921 A1 * | 10/2001 | Bonnefous | 600/437 |
| 2002/0136440 A1 * | 9/2002 | Yim et al. | 382/131 |
| 2005/0249327 A1 * | 11/2005 | Wink et al. | 378/8 |

OTHER PUBLICATIONS

Chen, Carroll and Hoffman, (ABSTRACT) 3d Reconstruction of Coronary Artery Tree from Biplane Angiograms, Abstracts from the 68th Scientific Sessions, p. I-599.

Chen, Hoffman and Carroll, (ABSTRACT) A 3D Coronary Processing Tool to Optimize Visualization Strategy in the Cardiac Catheterization laboratory, Abstracts from the 69th Scientific Sessions, p. I-437.

Chen and Carroll, Computer Assisted Coronary Intervention by Use of On-line 3D Reconstruction and Optimal View Strategy, Proceedings of the Medical Image Computing and Computer-Assisted Intervention, Cambridge, Mass.; Oct. 11-13, 1998, pp. 377-384.

Meier, Ziskin, Santamore and Bove, Kinematics of the Beating Heart, IEEE Transactions on Biomedical Enginerring, vol. BME-27, No. 6, Jun. 1980, pp. 319-329.

Puentes, Roux, Garreau, Coatrieux and Mora, Three-Dimensional Movement Analysis in Digital Subtraction Angiography: Symbol Generation from 3-D Optical Flow.

Parker, Pope, Van Bree and Marshall, Three-Dimensional Reconstruction of Moving Arterial Beds from Digital Subtraction Angiography, Computers and Biomedical Research, vol. 20., 1987, pp. 166-185.

Young, Hunter and Smaill, Epicardial Surface Estimation from Coronary Angiograms, Computer Vision, Graphics, and Image Processing, vol. 47, 1989, pp. 111-127.

Coppini, Demi, L'Abbate and Valli, Computational Geometry of Heart Surfaces, IEEE, 1989, pp. 293-296.

Young, Hunter and Smaill, Estimation of Epicardial Strain Using the Motions of Coronary Bifurcations in biplane Cineangiography, IEE Transactions on Biomedical Engineering, vol. 39, No. 5, May 1992, pp. 526-531.

Gross and Friedman, Dynamics of coronary artery curvature obtained from biplane cineangiograms, Journal of Biomechanics 31, 1998, pp. 479-484.

Wahle, Oswald and Fleck, A New 3-D Attributed Data Model for Archiving and Interchanging of Coronary Vessel Systems, German Heart Institute, Berlin, Germany, May 1993, pp. 603-606.

Dalaere, Smets, Suetens and Marchal, Knowledge-based System for the Three-Dimensional Reconstruction of Blood Vessels from Two Angiographic Projections, Medical and Biological Engineering Computing, Nov. 1991, pp. NS27-NS36.

Yanagihara, Haswhimoto, Sugahara and Sugimoto, A New Method for Automatic Identification of Coronary Arteries in Standard Biplane Angiograms, International Journal of Cardiac Imaging, 1994, pp. 253-261.

Liu and Sun, Fully Automated Reconstruction of Three-dimensional Vascular Tree Structures from Two Orthogonal Views Using Computational Algorithms and Production Rules, Optical Engineering, Oct. 1992, vol. 31, No. 10, pp. 2197-2207.

Wahle, Wellnhofer, Magaragu, Sauer, Oswald and Fleck, Assessment of Diffuse Coronary Artery Disease by Quantatative Analysis of Coronary Morphology Based upon 3-D Reconstruction from Biplane Angiograms, IEEE Transactions on Medical Imaging, Jun. 1995, vol. 14, No. 2, pp. 230-241.

Blais, G. et al., Registering Multiview Range Data to Create 3D Computer Objects, Aug. 1995, IEEE Transactions on Pattern Analysis and Machine Intelligence, vol. 17, No. 87, pp. 820-824.

Chen, Carroll and Hoffman, Three-Dimensional Reconstruction of Coronary Arterial Tree Based on Biplane Angiograms, Medical Imaging 1996—Image Processing, Proceedings SPIE—The International Society for Optical Engineering, Feb. 12-15, 1996, Newport Beach, California, vol. 2710, 13 pages.

Chen, Metz, Hoffman and Carroll, Improved Determination of Biplane Imaging Geometry and 3D Coronary Arterial Tree from Two Views, IEEE Computer Society Press Reprint—Reprinted from Proceedings of Computers in Cardiology 1994, Bethesda, Maryland, Sep. 25-25, 1994, 5 pages.

Carroll, Chen, Hellman and Hoffmann, (ABSTRACT) Improving Visualization Strategy for Coronary Interventions: The Utility and Need for 3-D Coronary Reconstruction, Oct. 15, 1996, vol. 94, No. 8, p. I-376.

Kawata, Niki and Kumazaki, Measurement of Blood Vessel Characteristics for Disease Detection Based on Cone-Beam CT Images, IEE Transactions on Nuclear Science, vol. 43, No. 6, Dec. 1996, pp. 3348-3354.

Peifer, Mullick, Ezquerra, Hyche, Klein and Cooke, Coronary Vasculature Visualization From Limited Angiographic Views, IEEE1990, pp. 195-200.

Kawata, Niki and Kumazaki, 3-D Image Reconstruction with Veiling Glare Correction to Improve the Contrast of 3-D Reconstructed Vascular Images, IEE Transactions on Nuclear Science, vol. 43, No. 1, Feb. 1996, pp. 304-309.

Chen and Carroll, 3-D Reconstruction of Coronary Arterial Tree to Optimize Angiographic Visualization, 23 pages.

Chen and Carroll, Dynamic Reconstruction of 3D Coronary Arterial Trees Based on a Sequence of Biplane Angiograms, Medical Imaging 1997,—Image Processing, Proceedings SPIE—The International Society for Optical Engineering, Feb. 25-28, 1997, Newport Beach, California, vol. 3034, pp. 358-368.

International Search Report, International Application No. PCT/US97/10194—Form PCT/ISA/210, pages 1-3.

Nguyen and skylansky, Reconstructing the 3-D Medical Axes of Coronary Arteries in Sinvle-view Cineangiograms, IEEE Transactions on Medical Imaging, Mar. 1994, vol. 13, No. 1, pp. 61-73.

Pellot, Herment, Sigelle, Horain, Maitre and Peronneau, A 3D Reconstruction of Vascular Structures from Two X-Ray Angiograms Using an Adapted Simulated Annealing Algorithm, IEEE Transactions on Medical Imaging, Mar. 1994, vol. 13, No. 1, pp. 48-60.

Gross, Mark F. et al., "Dynamics of coronary artery curvature obtained from biplane cineangiograms," Journal of Biomechanics, United States May 1998, vol. 31, No. 5, May 1998, pp. 479-484.

Pao, Y. C. et al., "Bending and twisting of an in vivo coronary artery at a bifurcation," Journal of Biomechanics, United States Mar. 1992, vol. 25, No. 3, Mar. 1992, pp. 287-295.

S.-Y. James Chen, John D. Carroll, John C. Messenger, Quantitative Analysis of Reconstructed 3-D Coronary Arterial Tree and Intracoronary Devices, IEEE Transactions on Medical Imaging, vol. 21, No. 7, Jul. 2002, pp. 724-740.

Zhaohua Ding, Hui Zhu, Morton H. Friedman, Coronary Artery Dynamics In Vivo, Annals of Biomedical Engineering, Pergamon Press, Oxford, GB, vol. 30, No. 4, 2002, pp. 419-429.

Robert Liao, S.-Y. James Chen, John C. Messenger, Bertron M. Groves, J.E.B. Burchenal, John D. Carroll, Four-Dimensional Analysis of Cyclic Changes in Coronary Artery Shape, Catheterization and Cardiovascular Interventions, Wiley-Liss, New York, NY, vol. 55, No. 3, 2002, pp. 344-354.

* cited by examiner

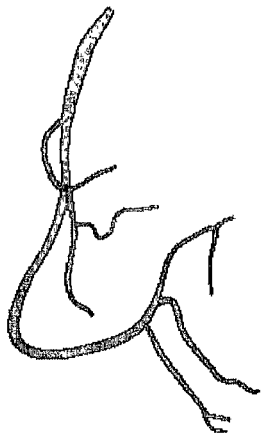 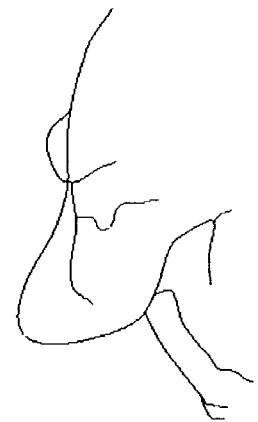
FIGURE 7a  FIGURE 7b
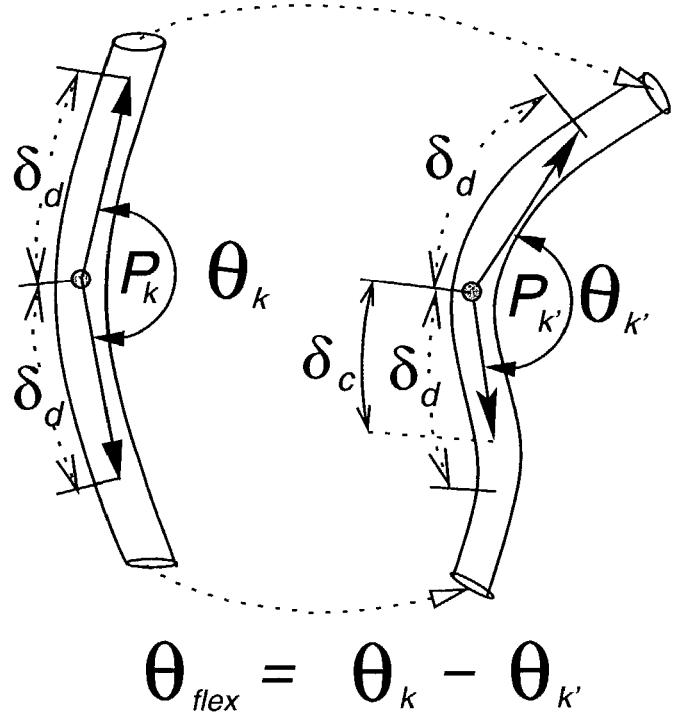
FIGURE 8

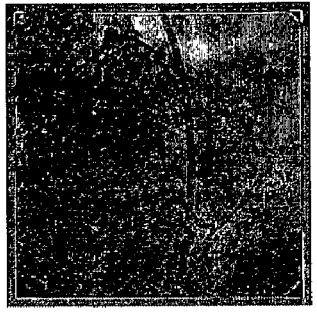
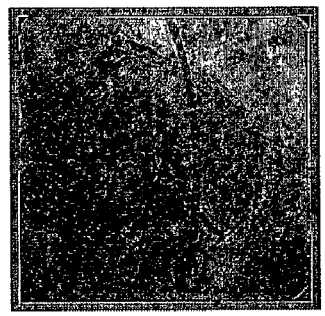
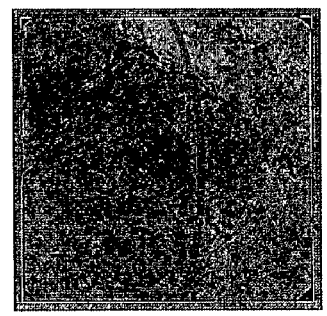
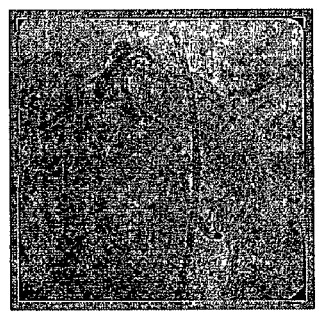
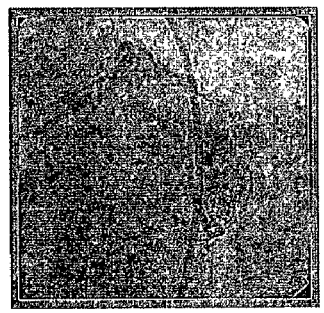
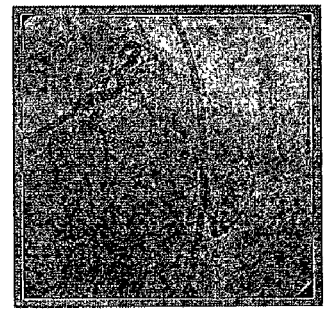
FIGURE 9a

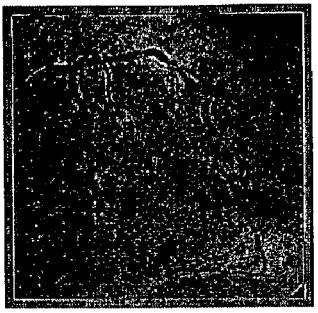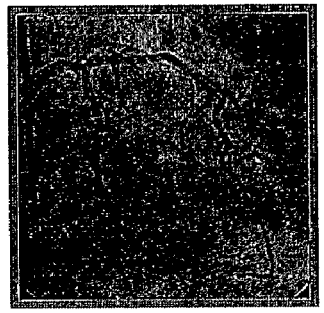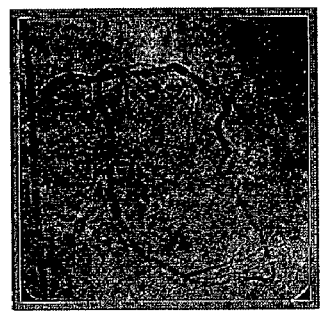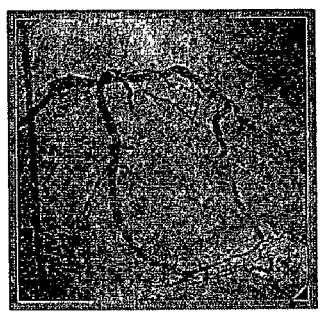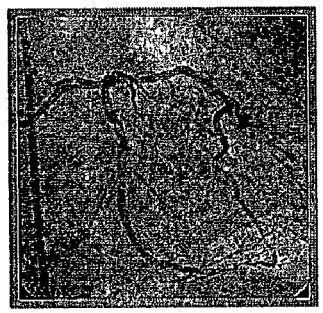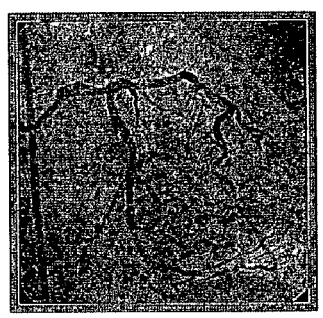
FIGURE 9b

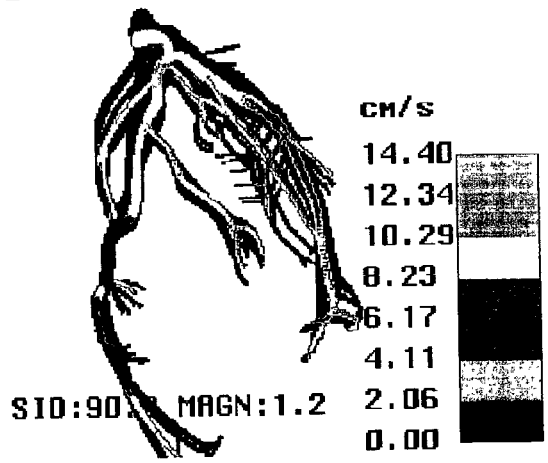
FIGURE 9g
FIGURE 9h
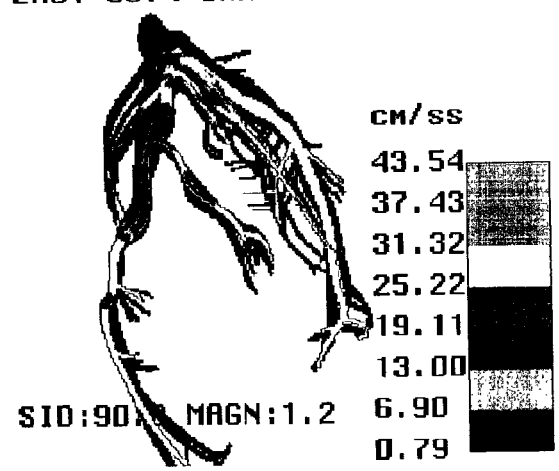

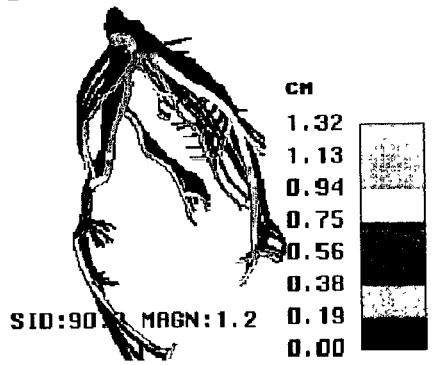
FIGURE 9i
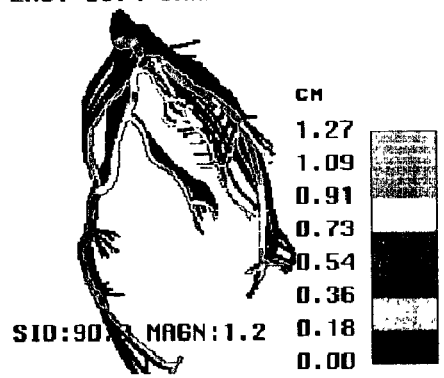
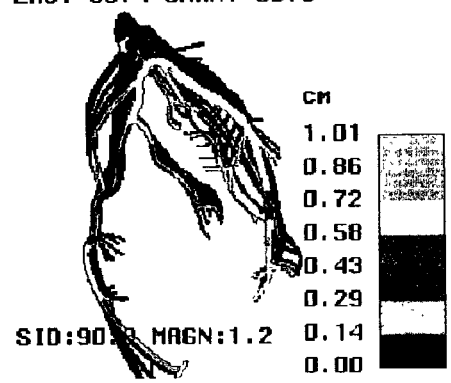

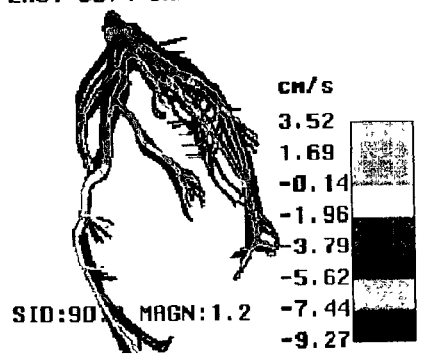
FIGURE 9j
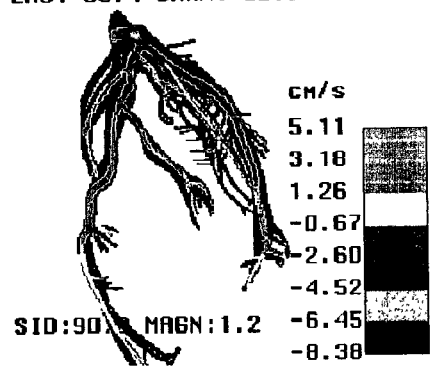
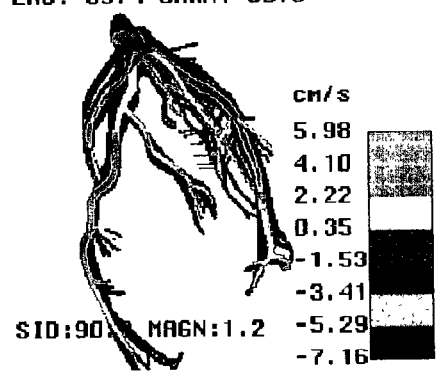

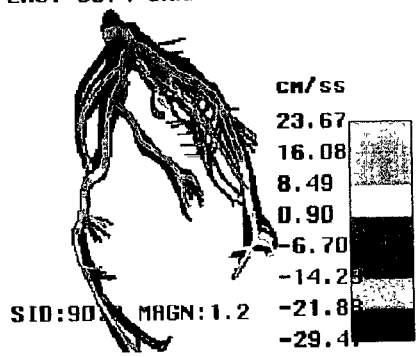
FIGURE 9k
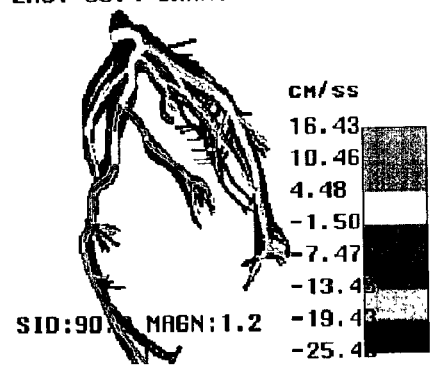
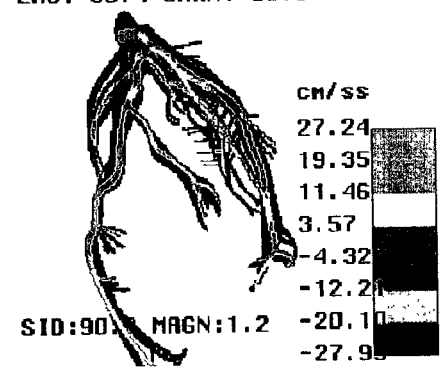

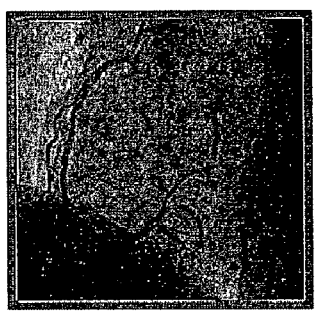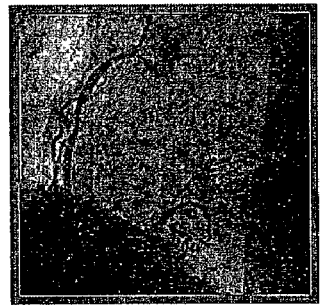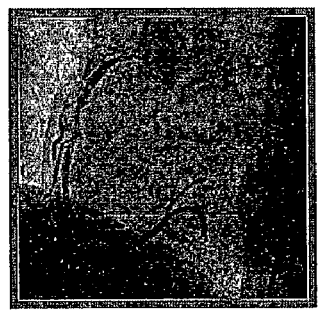
FIGURE 10a

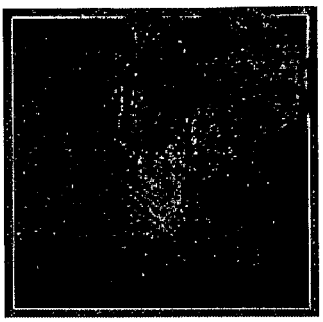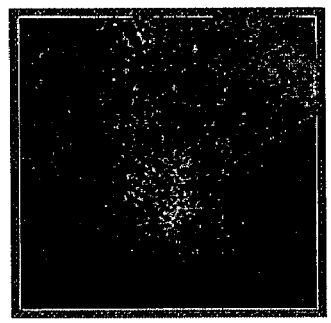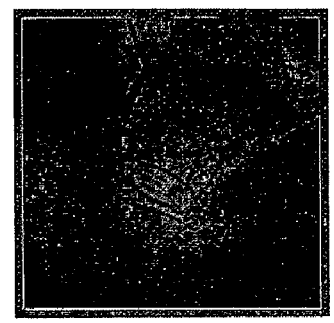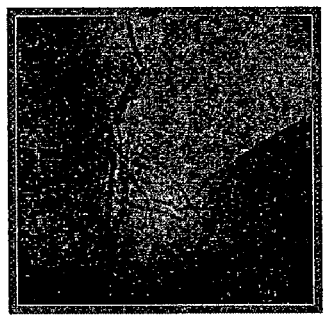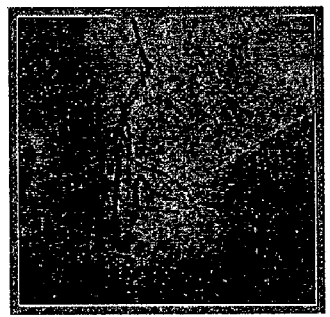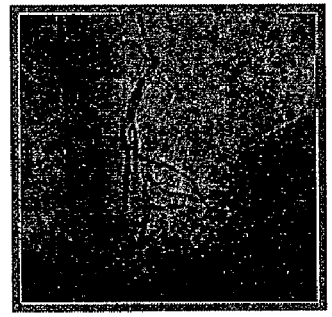
FIGURE 10b

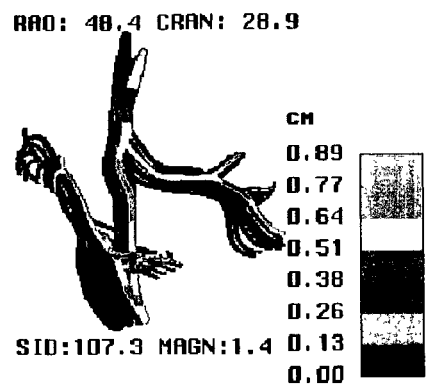
FIGURE 10i
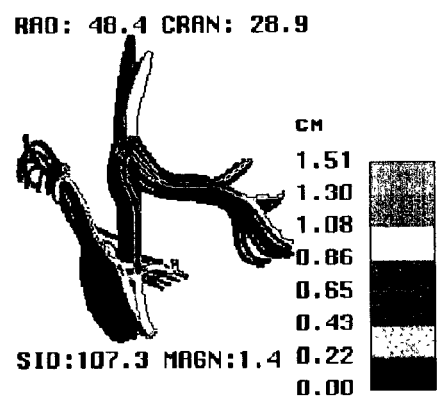
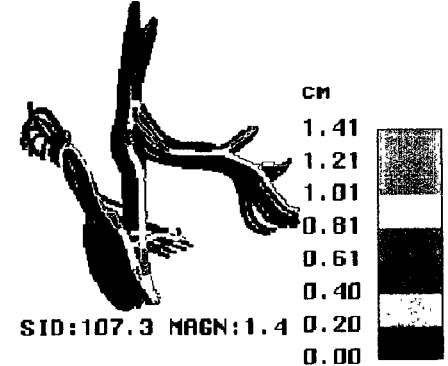

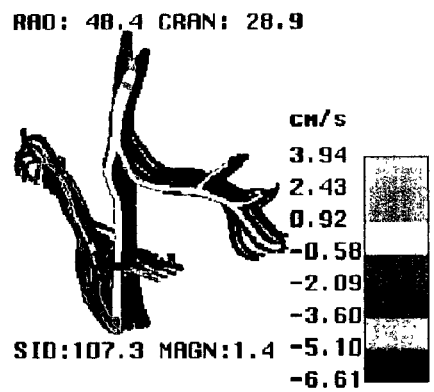
FIGURE 10j
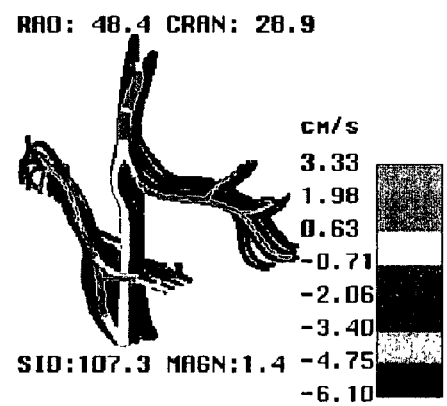
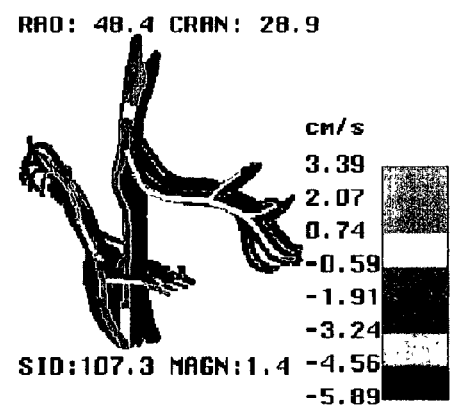

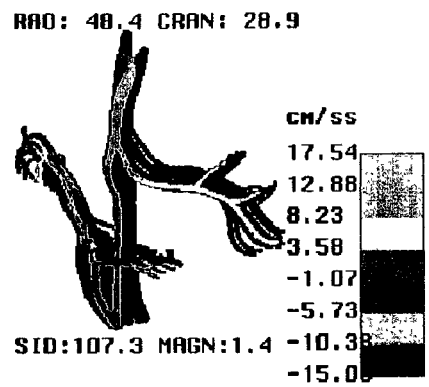
FIGURE 10k
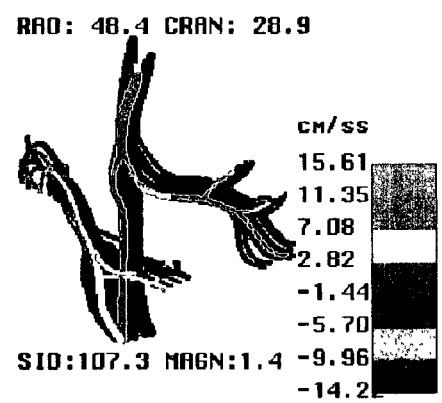
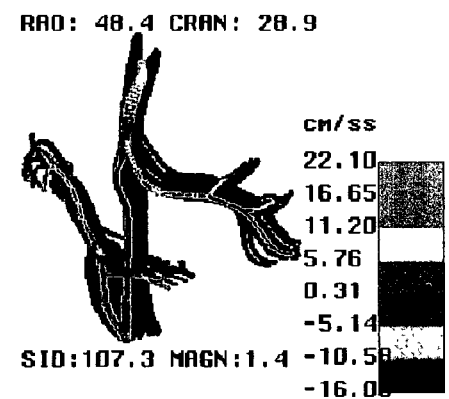

METHODS AND SYSTEMS FOR DISPLAY AND ANALYSIS OF MOVING ARTERIAL TREE STRUCTURES

GOVERNMENT LICENSE RIGHTS

The United States Government may own rights to the invention as research relevant to its development was funded by NIH Grant HL60220.

RELATED PATENT APPLICATIONS

This patent application is related to co-pending U.S. patent application Ser. No. 09/444,138, filed Nov. 20, 1999, which is hereby incorporated by reference.

BACKGROUND OF THE INVENTION

1. Field of the Invention

The present invention relates to reconstruction, a display and analysis of vascular tree structures and more specifically relates to reconstruction and of a moving cardiovascular tree structure from sequences of and geographic images and analysis of such a reconstructed moving model.

2. Discussion of Related Art

It is generally known in the art to display a reconstructed three-dimensional representation of a vascular tree structure from multiple two-dimensional radiographic images of the subject vascular tree structure. Co-pending patent application 09/444,138 teaches particular methods for accurately reconstructing a three-dimensional representation of a vascular tree structure from pairs of two-dimensional radiographic images each representing a view from a particular imaging angle. Such a three-dimensional reconstructed representation may be derived from, for example, a pair of images generated in a biplane radiographic imaging system or from a pair of images generated by a single plane radiographic imaging system positioned at each of two distinct viewing angles.

Such a three-dimensional reconstructed representation of a vascular tree structure is useful, as known in the art, for visualizing the vascular structure and for quantitative analysis of various measured attributes and parameters of selected portions of the vascular tree structure. For example, as discussed in co-pending patent application 09/444,138 such quantitative analysis and visualization is helpful for clinical procedures involving vascular implants and bypass procedures.

As presently practiced in the art, such visualization and quantitative analysis are applied only to a single, static frame of radiographic images—i.e., a snapshot in time. For example, biplane angiographs providing one static image of a coronary vascular structure in each of two viewing angles may be used to construct an accurate three-dimensional representation of the coronary vascular structure in one particular position corresponding to the static frame snapshot of the images. However, as commonly known in the art, vascular tree structures, especially coronary vascular structures, are in movement as blood is circulated through the structures.

In particular, coronary arteries and veins are dynamic, curvilinear structures that have a great degree of individual to individual variability and tortuosity. In the cardiovascular arena, percutaneous catheter-based interventional (i.e., therapeutic) procedures include a variety of coronary interventions, such as the placement of metal stents, atherectomy, radiation emitting catheters, devices to trap embolization of atherosclerotic debris, and placement of pacing electrodes in the coronary venous system. These procedures presently use two-dimensional X-ray based imaging as the sole or the major imaging modality for procedure guidance and quantification of key parameters. With the complex motions of the heart during each contraction, the degree of curvilinearity of coronary arteries undergoes a considerable change. Dynamic variations of coronary vascular curvilinearity have been very difficult to study because the forms of coronary angiographic imaging used clinically represent vascular structure only in two-dimensional format. Such a format does not provide anything but a rough semi-quantitative approach for studying the normal and changing curvilinearity of this coronary vascular tree and also limits the ability to quantify the degree of straightening caused by equipment transiently or permanently placed in coronary arteries during therapeutic procedures. Therefore, a quantitative description of coronary geometry and motion is required both for the mathematical modeling of arterial mechanics and for the evaluation and performance of a variety of current and emerging therapeutic procedures.

Some prior solutions have suggested coronary arterial movement analysis using bifurcation points or 3-D vessel centerlines of the coronary arterial tree. To facilitate the assessment of coronary arterial movements, it is necessary to recover the 3-D information of the coronary arterial tree throughout the cardiac cycle. These techniques provide limited analysis of a discrete set of points (the selected bifurcation points) of the arterial tree. Thorough analysis of the entire arterial tree, or arbitrary selected portions of the tree are not feasible when only discrete points are captured for analysis.

Other solutions suggest computer assisted techniques for estimation of the 3-D coronary arteries from biplane projection data have been reported. These methods were based on the known or standard X-ray geometry of projections, placement of landmarks, or the known vessel shape and on iterative identification of matching structures in two or more views. These reported techniques require a high degree of accuracy in the imaging equipment to record precise angles of imaging. Such accurate calibration is rare and generally not feasible in practical applications of such systems.

In another prior solution, a method based on motion and multiple views acquired in a single-plane imaging system was proposed. In these solutions, the motion transformations of the heart model consist only of rotation and scaling. By incorporation of the center-referenced method and initial depth coordinates and center coordinates, a 3-D skeleton of coronary arteries was obtained. This prior solution presumes a simplified model of the motion of the heart. In fact, cardiac movement is far more complex. Heart motion during contraction and relaxation actually involves five specific movements: translation, rotation, wringing, accordion-like motion, and movement toward to the center of chamber. The simplified model employed by this prior solution cannot therefore accurately model the true motion of the heart nor therefore of the cardiac arterial tree structure.

Other knowledge-based or rule-based systems have been proposed for 3-D reconstruction of coronary arteries by use of the model of a vascular network model. Because the rules or knowledge base were organized for certain specific conditions, it is not likely to generalize the 3-D reconstruction process to arbitrary projection data. These knowledge based systems utilize the knowledge of certain known heart conditions. These prior solutions do not therefore easily adapt to generalized aspects of cardiac motion nor to related arterial tree motion.

In yet another prior solution, the 3-D coronary arteries were reconstructed from a set of X-ray perspective projections by use of an algorithm from computed tomography. Due to the motion of heart, only a limited number of projections can be acquired. Therefore, accurate reconstruction and quantitative measurement are not easily achieved.

Closed-form solution of the 3-D reconstruction problem using a linear approach is suggested by still other prior solutions. Unfortunately, actual data are always corrupted by noise or errors and the linear approach based techniques may not be sufficiently accurate from noisy data.

In view of these various problems, optimal estimation has been explicitly investigated by still other prior solutions. A two-step approach has been proposed for an optimal estimation for a 3-D structure based on maximum-likelihood and minimum-variance estimation. Preliminary estimates computed by the linear algorithm were used as initial estimates for the process of optimal estimation. The second step to then refine the preliminary estimate can encounter mathematical problems if the preliminary estimate is too inaccurate as is often the case. In essence, the second refinement can get "trapped" in a sub-optimal mathematical solution by such an inaccurate preliminary estimate.

No presently practiced imaging techniques are known to provide for accurate reconstruction of a moving three-dimensional representation of a vascular tree structure. Neither is it presently known to provide for quantitative analysis of selected segments of such a reconstructed, moving three-dimensional representation of a vascular tree structure.

It is evident from the above discussion that a need exists for improved visualization and quantitative analysis techniques for reconstruction, display and analysis of a three-dimensional representation of a moving vascular tree structure. In particular, a need exists for improved techniques for visualizing and analyzing movements of a coronary vascular tree structure through a cardiac cycle from sequences of angiographic images.

SUMMARY OF THE INVENTION

The present invention solves the above and other problems, thereby advancing the state of the useful arts, by providing methods and associated systems for reconstructing, visualizing and analyzing a three-dimensional representation of a moving vascular tree structure from time varying sequences of radiographic images thereof. A broad purpose of the invention is to provide a novel patient-specific 4-D (e.g., 1-D in time varying space plus 3-D geometry) vascular model and to provide quantitative display tools to improve patient outcomes and enhance patient safety during, for example, percutaneous catheter-based interventions. In addition, these dynamic vascular trees can be displayed for an in-room advanced visual interface for the operator to better understand the target for intervention.

The invention broadly consists of three major processes (1) reconstruction of moving vascular tree throughout its motion cycle, (2) establishment of temporal correspondence with the smoothness constraints, and (3) kinematic and deformation analysis of the reconstructed 3-D moving vascular trees throughout its movement cycle.

Still more specifically, as applied to cardiovascular tree structures, the present invention provides methods and systems for reconstructing a moving coronary arterial tree throughout its cardiac cycle movement, establishment of temporal correspondence between sequences of imaging frames, and quantitative analysis of various kinematic and deformation measures of the reconstructed, displayed three-dimensional moving coronary arterial tree.

BRIEF DESCRIPTION OF THE DRAWINGS

This patent or patent application file contains at least one drawing executed in color. Copies of the patent or patent application publication with color drawing(s) will be provided by the Office upon request and payment of the necessary fee.

FIGS. 7a and 7b show a refined reconstructed arterial tree and a skeletal representation thereof, respectively.

FIG. 8 shows an exemplary global flexion analysis for a representative selected segment of a reconstructed arterial tree.

FIGS. 9a and 9b show two sequences of six images of an arterial tree for each of two viewing angles, respectively.

FIGS. 9c–9k show the color coded results of an exemplary 3-D reconstruction of the sequences of FIGS. 9a and 9b as deformation analysis and kinematic analysis.

FIGS. 10a and 10b show two sequences of six images of an arterial tree for each of two viewing angles, respectively.

FIGS. 10c–10k show the color coded results of an exemplary 3-D reconstruction of the sequences of FIGS. 10a and 10b as deformation analysis and kinematic analysis.

DETAILED DESCRIPTION OF THE PREFERRED EMBODIMENTS

Figure 1:
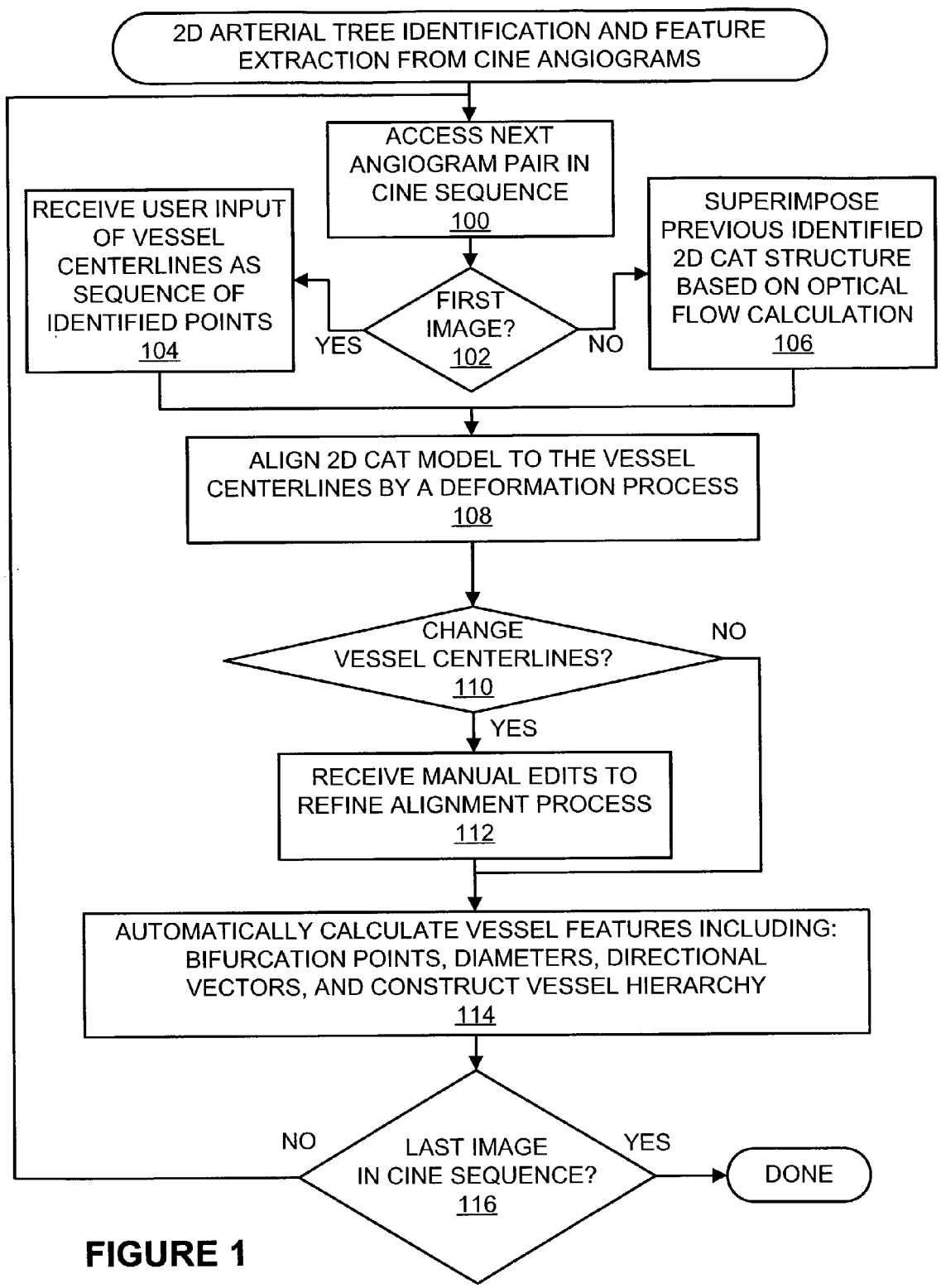
FIG. 1 is a flowchart describing the overall precessing of methods of the present invention.

Throughout this patent application, references are made to vascular and arterial tree structures as well as cardiovascular structures. As the terms relate to the present invention, all such vascular and arterial tree structures may be considered equivalent. Applications of the present invention are readily apparent in analysis of cardiovascular structures. Other applications for other vascular and arterial structures are similarly apparent to those of ordinary skill in the art. References herein to cardiac structures and motion should therefore be understood not as limitations on the application of the invention nor as limitations on the structures or methods of the claimed invention. Rather, all references to any particular vascular or arterial structure should be broadly understood to represent any arterial or vascular structure for which cine images of motion can be generated.

Reconstruction of Moving Coronary Arterial Tree

A first aspect of the present invention provides methods and associated systems for 3-D reconstruction of a vascular tree structure. Prior methods taught by co-pending patent application Ser. No. 09/444,138 are enhanced and extended herein to accurately reconstruct the moving coronary arterial trees throughout the cardiac cycle based on two sequences of cine angiograms acquired from a biplane or single-plane imaging system. The present reconstruction method broadly comprises four major steps: (A) acquisition of two angiogram sequences based on a single-plane or biplane imaging system, (B) identification of 2-D coronary arterial trees and feature extractions including bifurcation points, vessel diameters, and vessel directional vectors in the two image sequences, (C) determination of transformation in terms of a global $T_g$ and a local transformation $T_k$ matrices based on the identified vessel features, and (D) calculation of moving 3-D coronary arterial trees based on the transformations and extracted vessel features.

It will be readily recognized by those of ordinary skill in the art that the analysis aspects and features of the invention discussed herein below may be applied to a reconstructed 3-D representation of the moving arterial tree reconstructed according to any reconstruction technique. This particular reconstruction technique is therefore merely one possible reconstruction technique believed to generate an accurate 3-D representation of an arterial tree.

A. Image Acquisition

After routine cardiac catheterization is initiated, a standard coronary arteriogram may be completed in two standard views; one injection in a biplane system and two injections in a single plane imaging system. Such images may be acquired at a rate of 15 frames per second in each view throughout the cardiac cycle in each of the two views. The images may be selected with the aid of the superimposed electrocardiogram (ECG) signals and transferred to an appropriate personal computer or workstation for the 3-D reconstruction process. The images may be at a resolution of 512×512 matrix with a pixel color depth of one byte per pixel or any other desired resolution and pixel color depth.

Radiographic systems and methods are common for generating such images. However, those of ordinary skill in the art will recognize that numerous other imaging systems and methods may be employed to provide requisite 2-D images. For example, magnetic resonance imaging (MRI) systems and techniques generate images applying very different principles and methods. Computer tomography (CT) techniques and systems use computer image enhancement techniques to create 2-D images. All such sources of images are useful in association with the reconstruction aspects, features, methods and systems of the present invention.

B. Segmentation and Feature Extraction of 2-D Coronary Arterial Trees throughout the Cardiac Cycle An interactive, computer-based, semi-automatic system based on the technique of deformation model and segmentation may be employed as known in the art for the identification of the 2-D coronary arterial tree in the acquired angiograms. The required user interaction involves only the indication of several points inside the lumen, near the projection of each vessel centerline in the angiogram. After identifying such points, a spline-curve may be formed based on the selected points. The spline-curve may serve as the initial centerline of a corresponding vessel. An m by m operator (ridge operator) may be applied to convolve the given image by which the pixel is selected if it is a local minimum on intensity. By use of the deformation model, the identified pixels serve as the external forces to act on the initial model curve such that it will be gradually deformed and finally reside on the real centerline of the vessel.

Co-pending patent application Ser. No. 09/444,138 provides a detailed discussion of such processes of feature extraction for a single, static pair of angiograms.

The identified centerlines and the branching relationships may be used for construction of the vessel hierarchy in each angiogram by their labeling according to the appropriate anatomy and connectivity among the primary and secondary coronary arteries.

After the 2-D coronary arterial tree on the image acquired at the first time frame is obtained, it may be used as the initial 2-D arterial tree model for identification of the coronary arterial tree on the angiogram acquired at the next time frame. The ridge operator and deformable model may be employed as described previously such that the initial model curve is gradually aligned with the real centerline of vessel. Such a procedure may be performed iteratively to identify the 2-D coronary arterial trees with the associated coronary features in each angiogram sequences.

FIG. 1 is a flowchart depicting the 2-D feature extraction as an iterative process where the first image in the sequence of images may be used as an initial centerline approximation for the next image and so on for each image in the sequence. In particular, element 100 is first operable to access the next (first) image pair in the pair of cine angiogram sequences. Those of ordinary skill will understand, as noted elsewhere herein that cardiovascular structures are but one example of a useful application of such sequences of radiographic images. Numerous other examples of dynamic, moving vascular tree structures will be readily apparent to those of ordinary skill in the art. Element 102 then determines whether this image pair is the first in the sequence of images. If so, processing continues with element 104 to receive user input to identify a sequence of points and landmarks along the vascular tree 2D images to permit 3D reconstruction of the vascular structure at this first image pair from the sequence of time varying image pairs. Processing then continues as below with element 108. If element 102 determines that this is not the first image pair in the sequences of time varying image pairs, then element 106 is next operable to display the next pair of images in the time varying sequences superimposed with a 2D projection of the identified tree structure from the previous image pair with the identified points therefrom. Element 106 also receives user input to move the displayed point to new locations corresponding to the same points in the next time varying pair of images. Processing then continues with element 108.

Element 108 is then operable to align the 2D model of the present displayed pair of images according to the deformation discussed herein. Specifically, the 2D model is adjusted according to smoothness constraints and other constraints as discussed further herein below. Following the automatic deformation and smoothing of element 108, element 110 and 112 are operable to optionally receive user input to adjust the automatically determined projection. In particular, element 110 determines whether the user desires to make such adjustments and if so, element 112 receives user input to define any such adjustments.

Element 114 is then operable determine parameters of the reconstruction process (identify bifurcation points, vessel diameters and direction vectors) and to construct the 3D representation of the vascular tree corresponding to the present time varying image pair. Element 116 then determines if this was the last image in the time varying sequences of images. If not, the process continues by looping back to element 100 to process the next pair of images from the time varying sequences of images.

Figure 2A:
FIGS. 2a–2c respectively show an example of a manually identified 2-D coronary arterial tree superimposed to the corresponding image, the initially identified 2-D model corresponding thereto and the corresponding final 2-D coronary arterial tree.
Figure 2B:
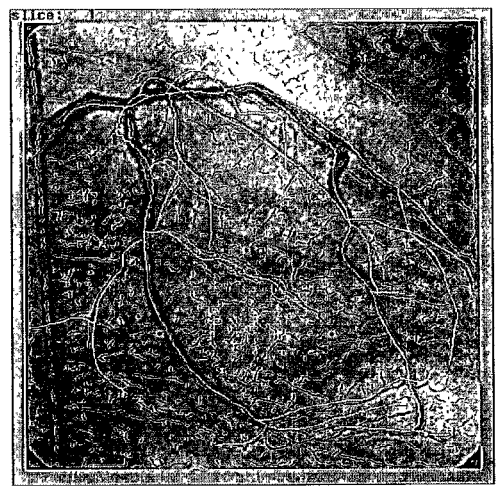
Figure 2C:
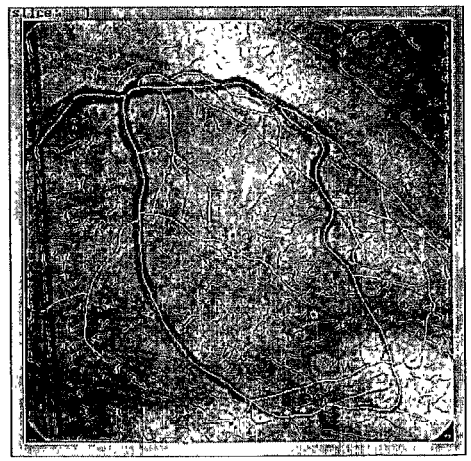

FIG. 2a shows an example of a manually identified 2-D coronary arterial tree superimposed to the corresponding image. FIG. 2b then shows this initially identified 2-D model (of FIG. 2a) superimposed to the next image in conjunction with the optical calculation. After the alignment and editing process, the final 2-D coronary arterial tree may be obtained as shown in FIG. 2c.

C. Determination of Transformations Characterizing Two Pairs of Angiographic Views By use of a biplane or single-plane system for image acquisitions, the spatial relationship between any two views can be characterized by a transformation in the forms of a rotation matrix R and a translation vector $\vec{t}$ with the X-ray source (or focal spot) served as the origin of 3-D coordinate space. In the first view, let $(u_i, v_i)$ denote the image coordinates of the i-th object point, located at position $(x_i, y_i, z_i)$. Therefore, $u_i = Dx_i/z_i$, $v_i = Dy_i/z_i$, where D is the perpendicular distance between the X-ray focal spot and the image plane. Let $(\xi_i, \eta_i)$ denote the scaled image coordinates, defined as $\xi_i = u_i/D = x_i/z_i$, $\eta_i = v_i/D = y_i/z_i$. The second projection view of the biplane imaging system can be describe in terms of a second pair of image and object coordinate systems u'v' and x'y'z' defined in an analogous manner. Scaled image coordinates $(\xi'_i, \eta'_i)$ in the second view for the i-th object point at position $(x'_i, y'_i, z'_i)$ are given by $\Xi'_i = u'_i/D' = x'_i/z'_i$, $\eta'_i = v'_i/D' = y'_i/z'_i$. The geometrical relationship between the two views can be characterized by $$\begin{bmatrix} x'_i \\ y'_i \\ z'_i \end{bmatrix} = R \cdot \left( \begin{bmatrix} x_i \\ y_i \\ z_i \end{bmatrix} - \vec{t} \right) = \begin{bmatrix} r_{11} & r_{12} & r_{13} \\ r_{21} & r_{22} & r_{23} \\ r_{31} & r_{32} & r_{33} \end{bmatrix} \cdot \begin{bmatrix} x_i - t_x \\ y_i - t_y \\ z_i - t_z \end{bmatrix}.$$

As in co-pending patent application Ser. No. 09/444,138, the transformation may be calculated based on the identified bifurcation points and direction vectors of the 2-D coronary arterial trees in each view. The required prior information (i.e., the intrinsic parameters of each single-plane imaging system) including: (1) the distance between each focal spot and its image plane, SID (focal-spot to imaging-plane distance), (2) the pixel size, $p_{size}$ (e.g., 0.3 mm/pixel), (3) the distance $\overline{ff'}$ between the two focal spots or the known 3-D distance between two points in the projection images, and (4) iso-center distance (with respect to which the rotary motion of the gantry arm rotates) relative to the focal spot. Given the set of 2-D bifurcation points and directional vectors extracted from the pair of images, an "optimal" estimate of the transformation and 3-D object point structures may be obtained by minimizing:

$$\min_{p,p',v,v'} F_1(P, P', v, v') =$$

$$\sum_{i=1}^{n} \left\{ \left( \xi_i - \frac{x_i}{z_i} \right)^2 + \left( \eta_i - \frac{y_i}{z_i} \right)^2 + \left( \xi'_i - \frac{x'_i}{z'_i} \right)^2 + \left( \eta'_i - \frac{y'_i}{z'_i} \right)^2 \right\} +$$

$$\|\vec{v}_i - [\vec{v}_i]_{xy}\|^2 + \|\vec{v}'_i - [\vec{v}'_i]_{x'y'}\|^2,$$

where n denotes the number of pairs of corresponding points extracted from the two images and P and P' denote the sets of 3-D object position vectors $\vec{p}_i = (x_i, y_i, z_i)$ and $\vec{p}'_i = (x'_i, y'_i, z'_i)$ respectively, $\vec{v}_i$ and $\vec{v}'_i$ denote the respective 2-D vessel directional vectors of bifurcations in each views, and $v = \{\vec{v}_1, \vec{v}_2, \ldots, \vec{v}_n\}$ and $v' = \{\vec{v}'_1, \vec{v}'_2, \ldots, \vec{v}'_n\}$ denote the projections of calculated 3-D vessel directional vectors of bifurcations in two views, respectively.

Figure 13:
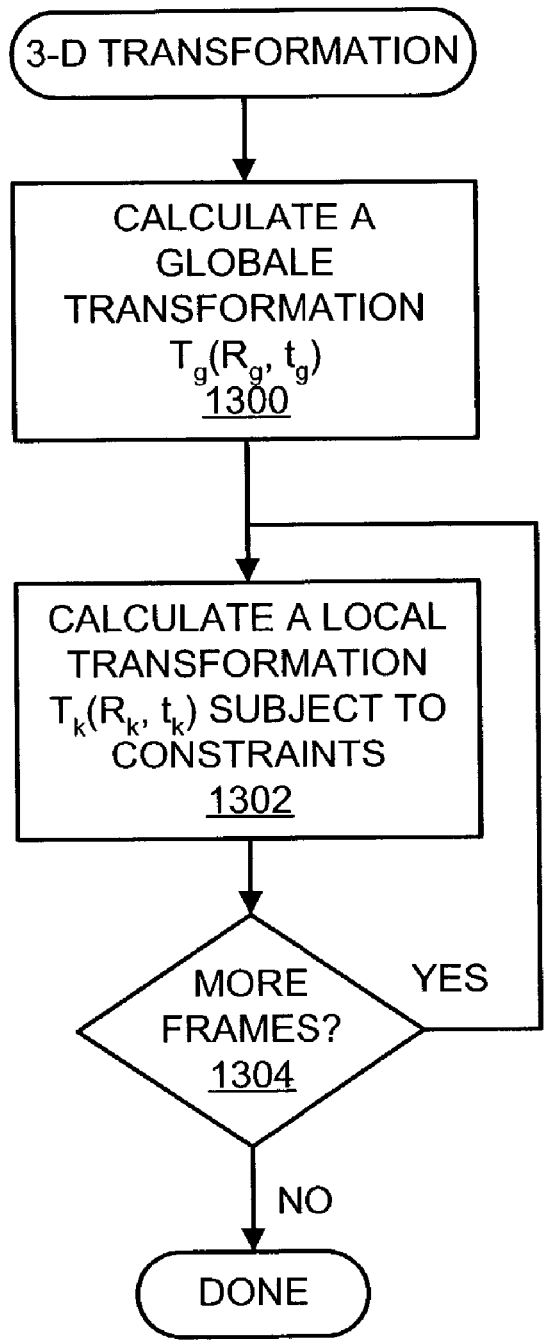
FIG. 13 is a flowchart of a method to determine a transformation matrix for each pair of images in a sequence of cine arteriograms.

A coarse-to-fine processing is employed to accurately determine the transformation associated with each pair of angiograms throughout the cardiac cycle. FIG. 13 is a flowchart describing a method of the present invention to determine a transformation for each pair of images. Element 1300 first determines a global transformation $T_g$ as discussed further herein below. Elements 1302 and 1304 are then iteratively operable to compute a local transform $T_k$ for each pair of images at time sequence index k. The transformations are determined as discussed herein below.

Let $\vec{p}^k_i = (x^k_i, y^k_i, z^k_i)$ denote the i-th bifurcation point, where $i = 1, \ldots, n_k$, identified in the first view acquired at the k-th time frame of m instances throughout the cardiac cycle, where $k = 1, \ldots, m$. Similarly, let $\vec{p}'^k_i = (x'^k_i, y'^k_i, z'^k_i)$ denote the i-th bifurcation point corresponding to $\vec{p}^k_i$ identified in the second view at the k-th time frame. Based on the corresponding bifurcation points and vessel directional vectors extracted from the cardiac cycle, the global transformation in terms of a rotation matrix $R_g$ and a translation vector $\vec{t}_g$ can then be calculated. Since the relationship between the two views can be characterized by a rotation matrix R and a translation vector $\vec{t} = [t_x, t_y, t_z]$ as shown in the above equations can be expressed as:

$$\min_{R_g, \vec{t}_g, p', v'} F_2(R_g, \vec{t}_g, P', v') =$$

$$\sum_{k=1}^{m} \sum_{i=1}^{n_k} \left( \xi'^k_i - \frac{x'^k_i}{y'^k_i} \right)^2 + \left( \eta'^k_i - \frac{y'^k_i}{z'^k_i} \right)^2 + \left( \xi^k_i - \frac{\vec{c}_1 \cdot \vec{p}'^k_i + t_x}{\vec{c}_3 \cdot \vec{p}'^k_i + t_z} \right)^2 +$$

$$\left( \eta^k_i - \frac{\vec{c}_2 \cdot \vec{p}'^k_i + t_y}{\vec{c}_3 \cdot \vec{p}'^k_i + t_z} \right)^2 + \|\vec{v}'^k_i - [R_g^{-1} \cdot \vec{v}'^k_i]_{xy}\|^2 + \|\vec{v}'^k_i - [\vec{v}'^k_i]_{x'y'}\|^2$$

where m denotes the number of time frames between the end-diastole and end-systole, $\vec{c}_k$ denotes the respective k-th column vectors of matrix $R_g$, $R_g^{-1}$ is the inverse matrix of $R_g$, and $[\vec{a}]_{xy}$ ($[\vec{a}]_{x'y'}$) denotes the projection of a 3-D vector a onto x-y (x'-y') plane.

The calculated $R_g$ and $\vec{t}_g$ are the estimates that characterize the two image sequences. When a biplane system is employed, each pair of angiograms may be acquired almost simultaneously throughout the cardiac cycle. Therefore, the global transformation is feasible to define each pair of images acquired from different time frames. When a single-plane system is adopted, the two image sequences may be acquired independently (i.e., two separate injections) corresponding to two different single cardiac cycles. Hence, the global transformation may not truly characterize every pair of images throughout the cardiac cycle; especially for those image pairs near the end-systolic time frame. By use of the global estimates, a refinement process is employed to calculate the new transformation in terms of $R_k$ and $\vec{t}_k = (t_{k_x}, t_{k_y}, t_{k_z})$ so that it can accurately characterize each individual pair of angiograms acquired at different time frames by minimizing:

$$\min_{R_k, \vec{t}_k, P'_k, v'_k} F_3(R_k, \vec{t}_k, P'_k, v'_k) =$$

$$\sum_{i=1}^{n_k} \left(\xi_i^{'k} - \frac{x_i^{'k}}{z_i^{'k}}\right)^2 + \left(\eta_i^{'k} - \frac{y_i^{'k}}{z_i^{'k}}\right)^2 + \left(\xi_i^k - \frac{\vec{c}_{k_1} \cdot \vec{p}_i^{'k} + t_x}{\vec{c}_{k_3} \cdot \vec{p}_i^{'k} + t_z}\right)^2 +$$

$$\left(\eta_i^k - \frac{\vec{c}_{k_2} \cdot \vec{p}_i^{'k} + t_y}{\vec{c}_{k_3} \cdot \vec{p}_i^{'k} + t_z}\right)^2 + \left\|\vec{\mu}_i^k - [R_k^{-1} \cdot \vec{v}_i^{'k}]_{xy}\right\|^2 + \left\|\vec{\mu}_i^{'k} - [\vec{v}_i^{'k}]_{x'y'}\right\|^2,$$

subject to the constraints $$\|R_k - R_g\| \leq \delta_{r_k}, \|\vec{t}_k - \vec{t}_g\| \leq \delta_{t_k}$$

where $\vec{c}_{k_j}$ denotes the respective j-th column vectors of matrix $R_k$, $\|R\|$ and $\|\vec{t}\|$ represent the matrix and vector norms, $\delta_{r_k}$ and $\delta_{t_k}$ denote the upper bounds of respective norms, $(\xi_i^k, \eta_i^k)$ and $\xi_i^{'k}, \eta_i^{'k}$ denote the 2-D bifurcation points extracted from the first and second views at the k-th time frame, respectively, $\vec{v}'_i^k$ and $\vec{p}'_i^k = (x'_i^k, y'_i^k, z'_i^k)$, i=1,2, . . . ,$n_k$, are the projections of calculated 3-D directional vectors and bifurcation points on the second view at the k-th time frame, and $\vec{v}_i^k$ and $\vec{v}'_i^k$ are the extracted 2-D directional vectors at the k-th time frame.

D. Calculation of 3-D Coronary Artery Skeleton

After the transformation $(R_k, \vec{t}_k)$ that defines every pair of two views in the image sequences was obtained, this information may be used to establish the point correspondences on each pair of 2-D vessel centerlines and calculate 3-D structures of coronary arterial tree. The transformation in conjunction with the epi-polar constraints and vessel hierarchy may be employed as the framework for calculation.

Figure 3:
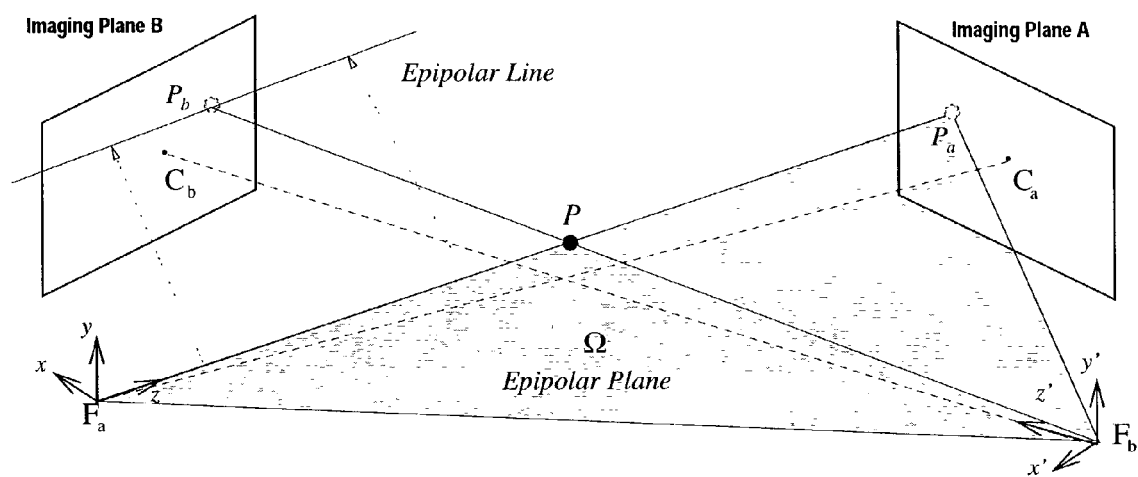
FIG. 3 depicts the determination of correspondences using the epi-polar plane.

Referring now to FIG. 3, if the relative orientations of two gantry angles are known (i.e., the locations of two focal spots $F_a$ and $F_b$ of the two images each having a center point $C_a$ and $C_b$, respectively), the correspondences of image points can be solved by use of "epi-polar constraints." As shown in FIG. 3, let P denote a 3-D point, and let $P_a$ and $P_b$, the projections of P, denote the pair of corresponding points in two images. Such constraints state that these points, $F_a$, $F_b$, $P_a$, $P_b$, and P, are all on one plane called the epi-polar plane as shown in FIG. 3. The epi-polar plane and each image plane intersect along a straight line called the epi-polar line (as labeled in FIG. 3). Therefore, the location of point $P_b$ in the second image must lie on the epi-polar line resulting from the intersection between the second image plane and the plane defined by point $P_a$ and the two focal spots.

Figure 4A:
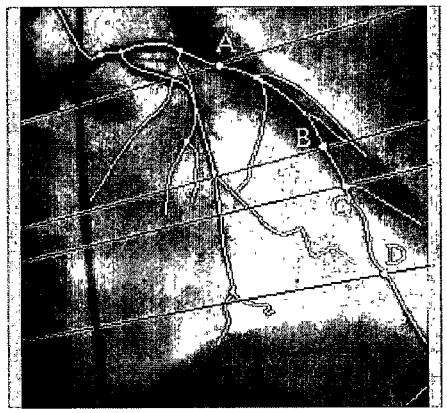
FIGS. 4a–4b depict corresponding points from two views.
Figure 4B:

A typical example of initial correspondence establishment by use of epi-polar constraints where points A, B, C, and D at the first view are defined by finding the intersections between the 2-D curve associated with left anterior descending artery (LAD) artery and respective epi-polar lines defined by a, b, c, and d at the second view as shown in FIGS. 4a and 4b. Specifically, FIG. 4a shows a first angiogram with four identified points: A, B, C and D. FIG. 4b shows the matching angiogram from another view angle with the corresponding four points a, b, c and d established by the initial correspondence.

Figure 5:
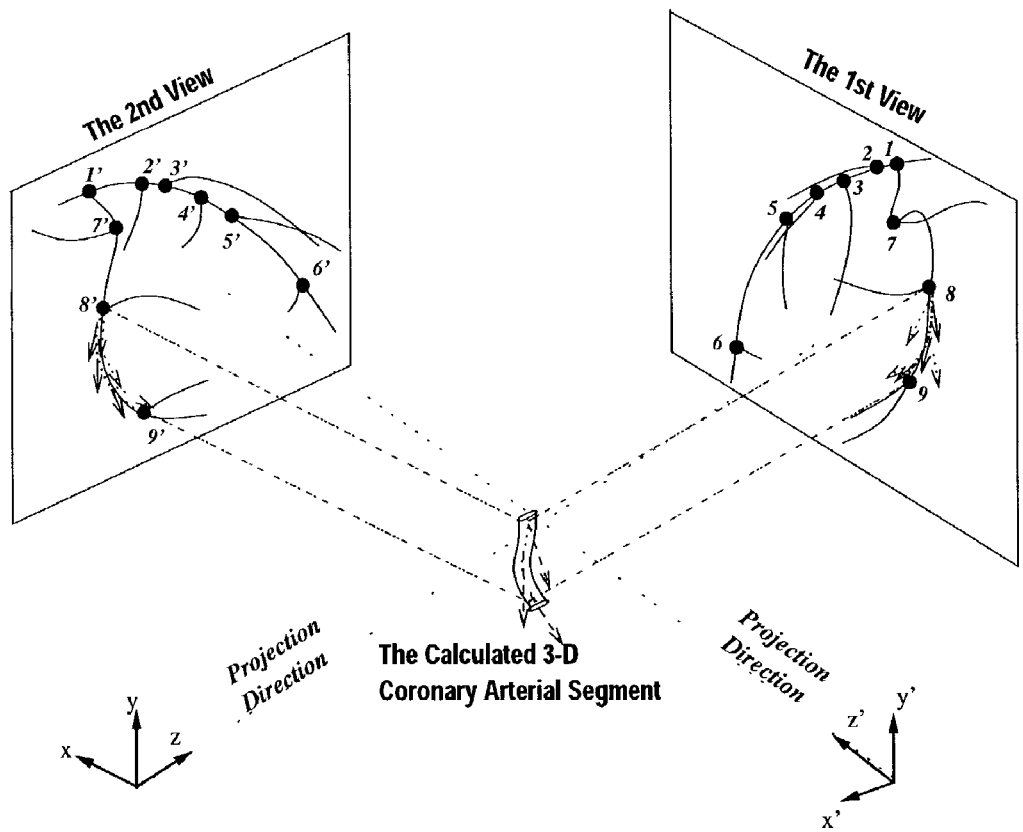
FIG. 5 shows a refinement process employed to calculate the refined correspondence using optimal parametric arguments.
Figure 14:
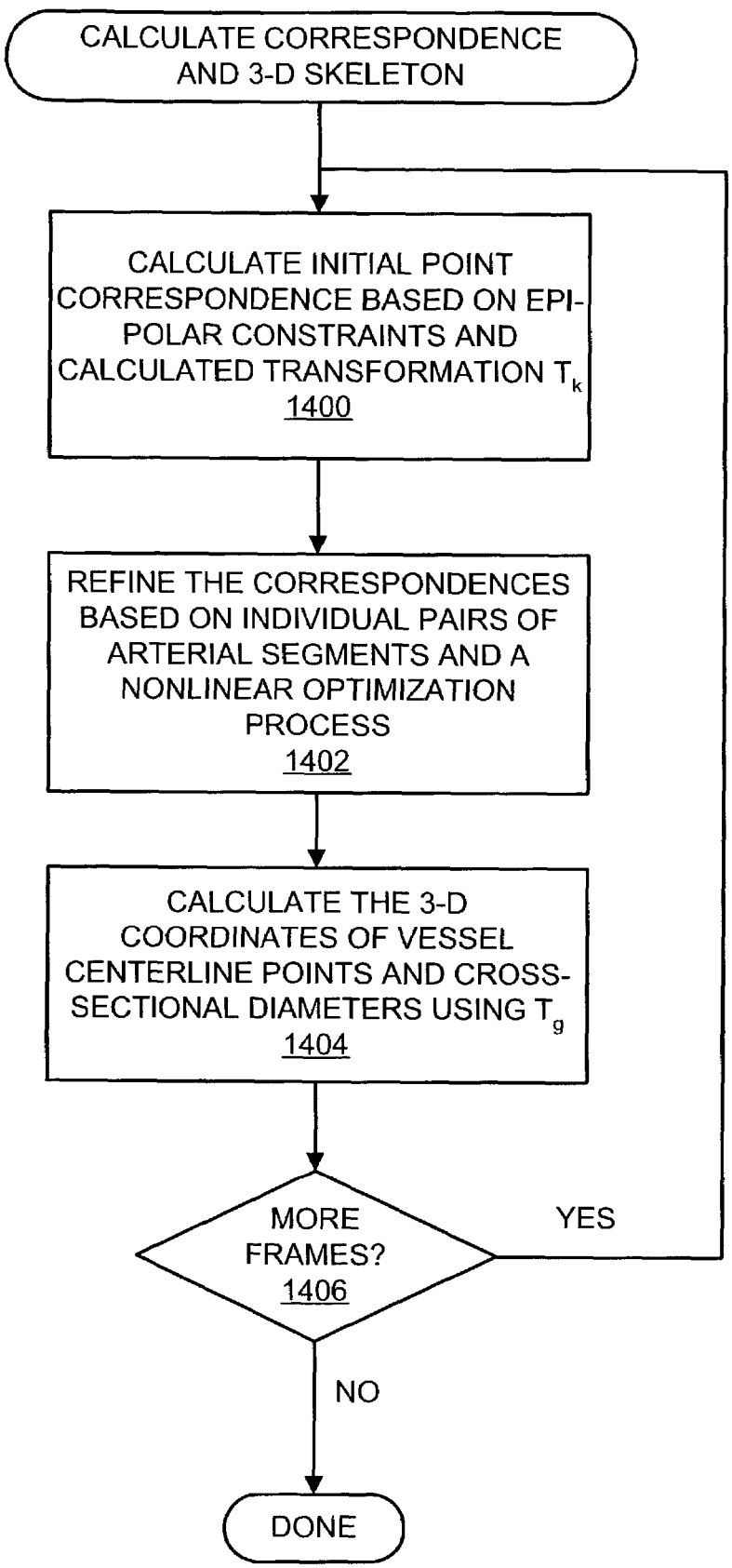
FIG. 14 is a flowchart describing a method to determine correspondences between images in a sequence of cine arteriograms.

When the epi-polar line is "tangential" relative to the 2-D vessel centerline curve, the accuracy of the calculated intersection point becomes sensitive to any small errors in epi-polar line derived based on the calculated transformation. To overcome the problem, a refinement process as shown in FIG. 14 may be employed. FIG. 14 provides a flowchart describing a method of the present invention to compute correspondences between points in each pair of images in the sequence. Element 1400 is first operable to calculate an initial point correspondence for the k-th pair of images based on epi-polar constraints and the corresponding transformation $T_k$. Element 1402 then refines the correspondences based on individual pairs of arterial segments and a nonlinear optimization. Element 1404 then refines the determination of vessel centerlines and diameters. Element 1406 causes the processing of elements 1400, 1402 and 1404 to repeat for each of the k time frames of the sequence. FIG. 5 shows a typical result of the refinement process employed to calculate the refined correspondence using optimal parametric arguments $s_1^k, s_2^k, \ldots s_{n-1}^k, s_{n_k}^k$ based on the following equation:

$$\min_{\hat{s}_k, P_k', v_k'} F_4(\hat{s}_k, P_k', v_k') =$$

$$\sum_{i=1}^{n_k} \left(\xi_i^{'k} - \frac{x_i^{'k}}{z_i^{'k}}\right)^2 + \left(\eta_i^{'k} - \frac{y_i^{'k}}{z_i^{'k}}\right)^2 + \left(f_x(s_i^k) - \frac{\vec{c}_{k_1} \cdot \vec{p}_i^{'k} + t_{k_x}}{\vec{c}_{k_3} \cdot \vec{p}_i^{'k} + t_{k_z}}\right)^2 +$$

$$\left(f_y(s_i^k) - \frac{\vec{c}_{k_2} \cdot \vec{p}_i^{'k} + t_{k_y}}{\vec{c}_{k_3} \cdot \vec{p}_i^{'k} + t_{k_z}}\right)^2 + \left\|f'(s_i^k) - [R_k^{-1} \cdot \vec{v}_i^{'k}]_{xy}\right\|^2 + \left\|\vec{v}_i^{'k} - [\vec{v}_i^{'k}]_{x'y'}\right\|^2,$$

where $$\hat{s}_k = \{s_1^k, s_2^k, \ldots, s_{n_k}^k\},$$

$$P_k' = \{\vec{p}_i^{'k} = (x_i^{'k}, y_i^{'k}, z_i^{'k}) | i = 1, \ldots, n_k\}, \text{ and } v_k' = \{\vec{v}_1^{'k}, \vec{v}_2^{'k}, \ldots, \vec{v}_{n_k}^{'k}\}$$

denote the set of parametric variables, the set of 3-D object position vectors, and the set of 3-D vessel directional vectors to be optimized, respectively, $n_k$ denotes the number of points of the 2-D vessel centerline at the k-th time frame, $(f_x(s_i^k), f_y(s_i^k))$ and $(\xi_i'^k, \eta_i'^k)$ are the respective spline-curve model and extracted 2-D vessel centerline points in two views, $$f'(s_i^k) = (f_x'(s_i^k), f_y'(s_i^k)) \text{ and } \vec{v}_i'^k$$

denote the respective spline-curve model and extracted 2-D directional vectors of vessel centerlines in each view, $$[R_k^{-1} \cdot \vec{v}_i'^k]_{xy} \text{ and } [\vec{v}_i'^k]_{x'y'}$$

denote the projection of the calculated 3-D directional vector on the respective image planes, $\vec{c}_{k,j}$, j=1,2,3, denotes the respective j-th column vectors of matrix $R_k$, and $R_k^{-1}$ is the inverse matrix of $R_k$ estimated at the k-th time frame. The 3-D position vectors $$P_k' \equiv \{\vec{p}_i'^k = (x_i'^k, y_i'^k, z_i'^k) | i = 1, \ldots, n_k\}$$

on vessel centerline are computed as indicated below where the 2-D pair correspondence $(\xi_i^k, \eta_i^k)$ are substituted by the 2-D spline-curve function $f(s_i^k)=(fx(s_i^k), fy(s_i^k))$. Based on the equations, the vessel centerline correspondences are globally established by incorporating the entire vessel shape in terms of directions and locations that will yield more accurate results than those obtained by only use of epi-polar constraints with local vessel segment points; especially when epi-polar line and vessel segment are tangential.

Figure 6A:
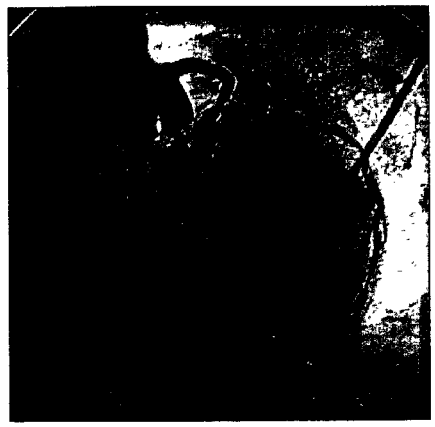
FIGS. 6a and 6b provide an exemplary pair of angiograms from two angles.
Figure 6B:
Figure 6C:
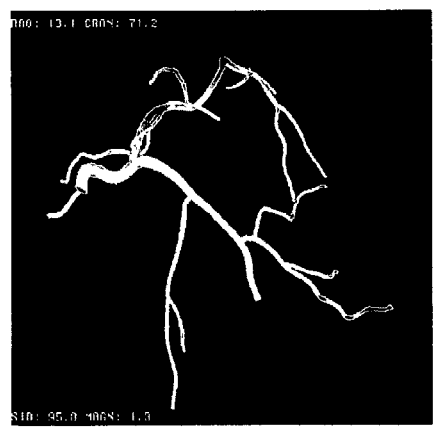
FIG. 6c shows a first reconstruction of the arterial tree represented by FIGS. 6a and 6b.
Figure 6D:
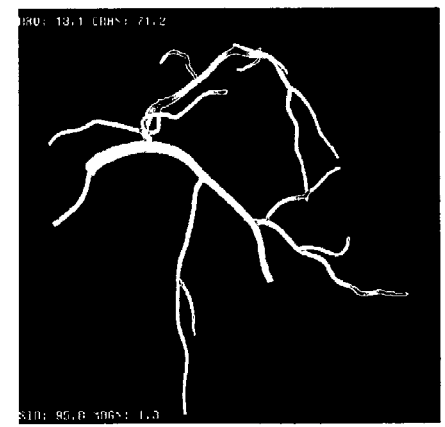
FIG. 6d shows a refined reconstruction of the arterial tree represented by FIGS. 6a and 6b.

FIGS. 6c and 6d show the results of 3-D left coronary arterial (LCA) reconstructed from a pair of angiograms as shown in FIGS. 6a and 6b based on the simple epi-polar technique and the refinement process, respectively. The reconstruction of left main artery apparently illustrates inaccurate results based on the simple epi-polar process (FIG. 6c) which are corrected after employing the refinement process (corrected as in FIG. 6d). The incorrect reconstruction of FIG. 6c is caused by the complete occlusion of the mid-LAD section of the first angiogram of the pair (i.e., FIG. 6a)

With the point correspondences on 2-D vessel centerlines $(\xi_j^k, \eta_j^k)$ and $$(\xi_j'^k, \eta_j'^k)$$

and the transformation $(R_k, \vec{t}_k)$ at the k-th time frame, the 3-D vessel centerline points of coronary arteries $(x_j^k, y_j^k, z_j^k)$'s can then be calculated based on the following equations:

$$[\vec{d}_1 \ \vec{d}_2 \ \vec{d}_3] \cdot \begin{bmatrix} x_j^k \\ y_j^k \\ z_j^k \end{bmatrix} = \begin{bmatrix} \vec{a}_k \cdot \vec{t}_k \\ \vec{b}_k \cdot \vec{t}_k \\ 0 \\ 0 \end{bmatrix},$$

where $$\vec{d}_1 = [r_{k_{11}} - r_{k_{31}}\xi_j'^k, r_{k_{21}} - r_{k_{31}}\eta_j'^k, 1, 0]^t$$

$$\vec{d}_2 = [r_{k_{12}} - r_{k_{32}}\xi_j'^k, r_{k_{22}} - r_{k_{32}}\eta_j'^k, 0, 1]^t$$

$$\vec{d}_3 = [r_{k_{13}} - r_{k_{33}}\xi_j'^k, r_{k_{23}} - r_{k_{33}}\eta_j'^k, -\xi_j^k, -\eta_j^k]^t$$

$$\vec{a}_k = \begin{bmatrix} (r_{k_{11}} - r_{k_{31}}\xi_j'^k) \\ (r_{k_{12}} - r_{k_{32}}\xi_j'^k) \\ (r_{k_{13}} - r_{k_{33}}\xi_j'^k) \end{bmatrix}, \vec{b}_k = \begin{bmatrix} (r_{k_{21}} - r_{k_{31}}\eta_j'^k) \\ (r_{k_{22}} - r_{k_{32}}\eta_j'^k) \\ (r_{k_{23}} - r_{k_{33}}\eta_j'^k) \end{bmatrix}$$

and $r_{k_{ij}}$ denotes the component of the rotational matrix $R_k$ at the k-th time frame.

After the 3-D vessel centerlines and lumen diameters are obtained, the anatomical morphology of coronary arterial tree can then be generated by a surface based reproduction technique. The 3-D lumen surface is modeled on the basis of a sequence of cross-sectional contours. Each contour $S_i$ along the vessel is represented by a $d_i$-mm circular disk centered at and perpendicular to the 3-D vessel centerline. The surfaces between every pair of consecutive contour $S_i$ and $S_{i+1}$ are generated based on a number of polygonal patches. With the modeled lumen surfaces, the morphology of reconstructed coronary arterial tree can be easily reproduced by employing well known techniques of computer graphics.

III. Establishment of Temporal Correspondence with Smoothness Constraints

The process of "temporal correspondence" may be performed to characterize the motion trajectory of every vessel centerline point on the coronary artery moving from the end-diastolic to the end-systolic time frames. The "minimal principles" in physics state that certain quantities are minimized when a physical process takes place. Such a theory led to the derivation of Hamilton's Principle which can be stated as follows: "Of all the possible paths along which a dynamic system may move from one point to another within a specified time interval (consistent with any constraints), the actual path followed is that which minimizes the time integral of the difference between the kinetic and potential energies". See for example, Y. C. Fung, *Foundations of Solid Mechanics*, Prentice-Hall Inc., Englewood Cliffs, N.J., 1965. Based on Hamilton's Principle, the problem of establishing temporal correspondence on each coronary artery can be modeled as searching the trajectory by which every artery spends minimal energy to change from its current position to a new position during contraction or relaxation and meanwhile maintains its shape similarity between every two consecutive time frames. Let k and k' denote the end-diastolic and end-systolic time frames, respectively. For every 3-D coronary arterial tree reconstructed at the two time frames, its j-th artery at end-diastolic time frame $l_j^k$ and at end-systolic time frame $l_j^{k'}$ can be modeled as a sequence of $n_k$ points $$P_j^k = \{P_{ij}^k = (x_{ij}^k, x_{ij}^k, z_{ij}^k,)\},$$

where i=1, . . . , $n_k$, and a sequence of $n_{k'}$ points $$P_j^{k'} = \{P_{ij}^{k'} = (x_{ij}^{k'}, y_{ij}^{k'}, x_{ij}^{k'},)\},$$

where i=1, . . . , $n_{k'}$, respectively. To assess coronary arterial deformation, the temporal correspondences of each pairs of 3-D coronary artery $l_j^k$ and $l_j^{k'}$ moving between the end-diastolic time frames k and end-systolic time frame k' must be established by using the equation as follows:

$$\min_{s_{ij}^{k'}} F_5(s_j^{k'}) = \sum_{i=1}^{n_k} \frac{1}{2} m_{ij}^k \left\{ \frac{[P_{ij}^k - f_{k'}(s_{ij}^{k'})]}{\Delta t_{k,k'}} \right\}^2 +$$

$$\frac{1}{2} K_{ij}^k \{|P_{ij}^k - P_{(i+1)j}^k| - |f_{k'}(s_{ij}^{k'}) - f_{k'}(s_{(i+1)j}^{k'})|\}^2 +$$

$$[T_{ij}^k - f_{k'}^{(1)}(s_{ij}^{k'})]^2 + [N_{ij}^k - f_{k'}^{(2)}(s)_{ij}^{k'}]^2,$$

subject to constraints $$0 \leq s_{1j}^{k'} \leq s_{2j}^{k'} \leq \ldots \leq s_{nkj}^{k'} \leq 1,$$

and $$f_k(t_{xj}^{k'}) = P_{xj}^{k'}, x = 1, 2, \ldots, n_{k'},$$
$$0 \leq t_{1j}^{k'} \leq t_{2j}^{k'} \leq \ldots \leq t_{nk'j}^{k'} \leq 1,$$

where $$m_{ij}^k \text{ and } K_{ij}^k$$

denote the mass and module of elasticity at the arterial segment $$P_{ij}^k,$$

respectively. The symbol $\Delta t_{k,k'}$ is the elapsed time between the k-th and k'-th time frames. The function $$f_{k'}(t_{xj}^{k'})$$

defines the 3-D artery $l_j^{k'}$ passing through the vessel centerline points $$P_{xj}^{k'}.$$

The symbol $$s_j^{k'} = \{s_{1j}^{k'}, s_{2j}^{k'}, \ldots, s_{nk_j}^{k'}\}$$

denotes the set of parametric variables corresponding to the 3-D vessel centerline points of the artery $$l_j^{k'} \cdot T_{ij}^k \text{ and } N_{ij}^k$$

denote the tangent and normal vectors at point $$P_{ij}^k.$$

The parametric curve function $$f_k, (s_j^{k'})$$

defines the centerline points of the artery $l_j^k$. Similarly, $$f_{k'}^{(1)}(s_j^{k'})$$

and $$f_{k'}^{(2)}(s_j^{k'})$$

denote the respective first and second derivatives of parametric curve function $$f_{k'}(s_j^{k'}).$$

By assuming the uniform material density, the mass associated with each vessel centerline point is approximately proportional the area of cross section $$(\text{i.e. } m_{ij} \propto d_{ij}^2).$$

The module of elasticity at one vessel centerline point is defined to be inverse proportional to the area of the cross section (i.e., $K_{i,j} \propto 1/d_{i,j}^2$).

Numerous standard mathematics library functions are readily available to those of ordinary skill in the art. For example, the subroutines ve17 and vf13 of *Harwell Subroutine Library* may be employed to solve the above equation. (*Harwell Subroutine Library*, vol. ½, AEA Technology, Harwell Laboratory, Oxfordshire, England, December 1995).

The first term in the above minimization equation defines the required minimal kinetic energy due to motion and the second term characterizes the minimal change in potential energy due to arterial segment stretching or foreshortening between k and k' time frames. The local shape similarity between the two coronary arteries is characterized based on the last two terms by minimizing the total angle differences of tangent and normal vectors at every pair of corresponding points on the respective arteries. On the basis of the above minimization, the temporal correspondence of vessel centerline points between any two time frames (e.g., end-diastole and end-systole) can be established.

A regularization solution may be obtained by minimizing an energy of the following form $$E(f) = \sum_{i \in A} [f(xi) - d(xi)]^2 + \lambda \int_a^b [f^{(n)}(x)]^2 dx$$

where A is a set of indices to the sample data points, $x_i$'s are the locations of the data points, $\lambda \leq 0$ is a weighting factor and $n \leq 1$ is an integer number. The first term on the right hand side, called the closeness term, imposes the constraint from the data d. The second term, called the smoothness term or the regularizer, imposes the a priori smoothness constraint on the solution. It is desired to minimize both but they may not be each minimized simultaneously. The two constraints are balanced by $\lambda$. Any $f$ minimizing the above equation may be a smooth solution in the so-called Sobolev space $W_2^n$. In the Sobolev space, every point of $f$ is a function whose (n−1) derivative is absolutely continuous and whose n-th $f^{(n-1)}$ derivative $f^n$ is square integrable. Different types of regularizer impose different types of smoothness constraints. The employed smoothness constraints function is a Bézier surface function S(u, v) that is formed as the Cartesian product of Bézier blending functions:

$$S(u,v) = \sum_{j=0}^{m} \sum_{l=o}^{n} P_{j,l} B_{j,m}(u) B_{l,n}(v), 0 \leq u, v \leq 1,$$

with $P_{j,l}$ specifying the location of the (m+1) by (n+1) control points and subject to the constraints $$\sum_{i=0}^{n_s} \sum_{k=o}^{n_c} \Psi(S(u,v), p_{s_i}^k) < \lambda_s,$$

where $$p_{s_i}^k = (x(s_i^k), y(s_i^k), z(s_i^k))$$

denote the $n_s+1(n_s>n)$ moving vessel centerline points at individual $n_c+1(n_c>m)$ time frames, $\Psi(S, p)$ denotes the distance between the point p to the surface function S, and $\lambda_s \leq 0$ is a constraints relaxation factor.

$B_{j,m}(u)$ and $B_{l,n}(v)$ are polynomial functions of degree one less than the number of control points used (i.e., at least a third order derivative function) and may be defined as $$B_{j,m}(u) = C(m,j)u^j(1-u)^{m-j}$$

$$B_{l,n}(v) = C(l,n)v^n(1-v)^{l-n}$$

and the C(m,j) and C(l,n) represent the binomial coefficients $$C(m,j) = \frac{m!}{j!(m-j)!}, C(l,n) = \frac{l!}{n!(l-n)!}.$$

IV. Kinematic and Deformation Analysis of Moving Coronary Arterial Tree

As noted above, the analysis features and aspects of the present invention may be applied to any reconstructed 3-D representation of an arterial tree structure. The above-identified methods and structures for such reconstruction and smoothing are but one exemplary technique believed to generate highly accurate representations of the arterial structure. Numerous other methods and structure for generating such a 3-D representation will be readily apparent to those of ordinary skill in the art. In particular, rotational angiography systems and techniques are rapidly developing that are capable of generating 3-D representations of moving arterial tree structures.

The skeleton of a reconstructed 3-D vessel may be mathematically defined as a curve function $\rho(s)=(x(s), y(s), z(s))$ connecting all the 3-D centerline points. A right coronary arterial (RCA) tree shown in FIG. 7a as a full 3D reconstruction and in and 7b as a skeleton structure, where $0 \leq s \leq 1$ is the parametric variable. The employed parametric function is a Bézier curve $\rho(s)$ that is formed as the Cartesian product of Bézier blending functions:

$$\rho(s) = \sum_{j=0}^{m} p_j B_{j,m}(s), 0 \leq s \leq 1,$$

subject to the constraints $\rho(s_i)=(x(s_i), y(s_i), z(s_i))$, $0 \leq s_i \leq 1, i=0, 1, \ldots, n_s$, where $\rho(s_i)$, $i=0, \ldots, n_s$, with $(n_s+1) \geq 4$, denotes the individual vessel centerline points, and $p_j$, $j=0, \ldots, m$, denote the (m+1) control points with $n_s \geq m \geq 3$. The employed constraints ensure that the derived curve function will pass through the vessel centerline points. $B_{j,m}(s)$ is a polynomial function of degree one less than the number of control points used (i.e., at least a third order derivative function) and is defined as above.

A. Motion Analysis

Based on the calculated parametric variables and function in the above equations, a trajectory of vessel centerline point can be defined by a function $r_{ij}(u)$ on the basis of a Bêzier curve as follows:

$$r_{ij}(u) = \sum_{g=0}^{m} P_{ij}^g B_{g,m}(u), \ 0 \leq u \leq 1,$$

subject to the constraints $$r_{ij}(u_k) = (x(u_k), y(u_k), z(u_k)) = f_k(s_{ij}^k),$$
$$0 \leq u_k \leq 1, k = 0, 1, \ldots, (n_c - 1),$$

where $r_{ij}(u_k)$, $k=0, \ldots, (n_c-1)$, with $nc \geq 4$, denotes the i-th vessel centerline point $$f_k(s_{ij}^k)$$

of the j-th vessel in the coronary artery tree moving throughout nc time frames during the cardiac cycle, and $$p_{ij}^g, g = 0, \ldots, m,$$

denote the m+1 control points with $n_c \geq m \geq 3$. The employed constraints ensure that the derived curve function will pass through the vessel centerline pont moving through the spatial domain. $B_{g,m}(u)$ is a polynomial function of degree one less than the number of control points as described in the above equations.

The displacement vector $$D_{ij}^{k+1}$$

which define the arterial movement of the 3-D vessel centerline point between the k-th and (k+1)-th time frames can be easily calculated as $$D_{ij}^{k+1} = f_{k+1}(s_{ij}^{k+1}) - f_k(s_{ij}^k) \text{ with } P_{ij}^0 = f_0(s_{ij}^0).$$

On the basis of the path function $$r_{ij}(u), r_{ij}^{(1)}(u) \text{ and } r_{ij}^{(2)}(u)$$

can be derived that define two other motion parameters in terms of velocity and acceleration for every vessel centerline point as $$r_{ij}^{(1)}(u) = \sum_{g=0}^{m} p_{ij}^g \frac{(g - mu)}{u(1 - u)} B_{g,m}(u), \ 0 \leq u \leq 1,$$

$$r_{ij}^{(2)}(u) = \sum_{g=0}^{m} p_{ij}^g \frac{(g - mu)^2 - mu^2 - g(1 - 2u)}{u^2(1 - u)^2} B_{g,m}(u)$$

subject to the constraints $$r_{ij}(u_k) = (x(u_k), y(u_k), z(u_k)) = f_k(s_{ij}^k),$$
$$r_{ij}^{(1)}(0) = 0, r_{ij}^{(1)}(1) = 0, 0 \leq u_k \leq 1, k = 0, 1, \ldots, (n_c - 1).$$

An alternate evaluation for the n-th derivative at u=0 is given by $$r_{ij}^{(n)}(0) = \frac{m!}{(m-n)!} \sum_{g=0}^{} n(-1)^{r-g} \frac{n!}{g!(n-g)!} p_{ij}^g,$$

and at u=1 by $$r_{ij}^{(n)}(1) = \frac{m!}{(m-n)!} \sum_{g=0}^{} n(-1)^g \frac{n!}{g!(n-g)!} p_{ij}^{m-g}.$$

B. Local Deformation Analysis

By use of such a spline-based curve modeling technique, one is able to apply the theory of differential geometry such as Frenet-Serret apparatus (F-S theory) or its variation to study the geometrical nature of the 3-D coronary artery or intracoronary device at any time frame during the cardiac cycle. See for example, R. S. Millman and G. D. Parker, *Elements of Differential Geometry*, Prentice-Hall Inc., Englewood Cliffs, N.J., 1977. A technique based on the F-S theory of differential geometry has been developed to study the geometrical nature or tortuosity of the 3-D coronary artery shape at any time frame in the cardiac cycle. The F-S theory consists of five components: three vector fields along the given curve (the tangent $T(s)$, the normal $N(s)$, and the bi-normal $B(s)$ vectors) and two scalar valued functions (the curvature $\kappa(s)$ and the torsion $\tau(s)$) where s denotes the parametric variable defining the location of point on the curve function(s). The curvature $\kappa(s_0)$ measures the rate of change of the angle defined by the two neighboring tangents $T(s_0)$ and $T(s_0+\delta_s)$ associated with the two points $\rho(s_0)$ and $\rho(s_0+\delta_s)$. In other words, it characterizes the degree of bending pertinent to a local curve segment in the neighborhood between $s_0$ and $s_0+\delta_s$ (i.e., how rapidly the curve pulls away from the plane n perpendicular to the tangent vector at $T(s_0)$). Similarly, the torsion at $\tau(s_0)$ measures a rate of change (or twisting) at a point $\rho(s_0)$ how its trajectory twists out of the plane $\Omega_t$ perpendicular to the normal vector $B(s_0)$).

The calculation of curvature and torsion at every vessel centerline point $s_0$ is characterized by the following equations:

$$T(s_0) = \frac{\rho^{(1)}(s_0)}{|\rho^{(1)}(s_0)|}$$

$$B(s_0) = \frac{\rho^{(1)}(s_0) \times \rho^{(2)}(s_0)}{|\rho^{(1)}(s_0) \times \rho^{(2)}(s_0)|}$$

$$N(s_0) = B(s_0) \times T(s_0)$$

$$k(s_0) = \frac{|\rho^{(1)}(s_0) \times \rho^{(2)}(s_0)|}{|\rho^{(1)}(s_0)|^{(3)}}$$

$$\tau(s_0) = \frac{[\rho^{(1)}(s_0) \times \rho^{(2)}(s_0)] \cdot \rho^{(3)}(s_0)}{|\rho^{(1)}(s_0) \times \rho^{(2)}(s_0)|^{(2)}},$$

where $\rho^{(i)}(s)$ denotes the i-th derivative with respect to s. Generally, the above equations define a microscopic approach to look in very small neighborhoods of points. Therefore they are regarded as primitives for assessing the local geometrical property of a curve.

C. Global Flexion Analysis

The analysis may be performed by comparing the coronary trees reconstructed at two different time frames k and k'. The enclosed angle $\theta_k$ ($\theta_{k'}$) may be defined as the angle formed by two chords that extend from a point along the centerline to the location with the minimal length between a pre-defined length $\delta_d$ (e.g., 5 mm) and the next local minimal curvature $\delta_c$ in each direction as shown in FIG. 8. The enclosed angle may be calculated for every point of the centerlines between the two time frames. The flexion angle $\theta_{flex}$ is calculated as the difference between $\theta_k$ and $\theta_{k'}$ (i.e., $\theta_{flex} = \theta_k - \theta_{k'}$) for every vessel centerline point. The local maximum with the value greater than a threshold σ (e.g., 15 degrees) is marked as a flexion point (FP) with bending movement. Similarly, the local minimum with the value less than a threshold −σ (e.g., −15 degrees) is marked as a flexion point (FP) with straightening movement. Note that the threshold value can be chosen dynamically within a range (e.g., 7.5 degrees–45 degrees) such that different sets of FPs can be calculated.

D. Dynamic Rendering

The kinematic and deformation measurements $r_{ij}$, $r^{(1)}_{ij}$, $r^{(2)}_{ij}$, $\kappa(s)$, $\tau(s)$ and $\theta_{flex}$ may be color coded on the lumen of moving coronary arterial tree. Seven colors (red, orange, yellow, green, blue, cyanic, and purple) may be used to represent the magnitudes of each kinetic measurement. The magnitude of each measurement throughout the cardiac cycle are divided into 7 sub-regions corresponding to each color where the red color denotes the largest magnitude and purple color represents the smallest magnitude. Those of ordinary skill in the art will recognize that any number of colors and gradations of colors may be used to represent the dynamic measures.

V. Exemplary Results

Figure 9C:
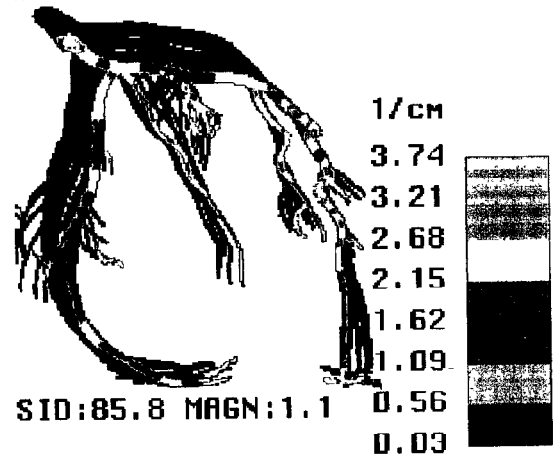

In FIGS. 9a and 9b, an example is shown of a pair of left coronary cine angiograms acquired between end-diastole and end-systole using a single-plane imaging system. Specifically, FIG. 9a is a sequence of six (6) from a first angle of a single plane imaging system and FIG. 9b is a second sequence of six (6) images from a different angle of the same single plane imaging system. Both image sequences cover (in six frames) an entire cardiac cycle of the movement of the coronary arterial tree. FIGS. 9c through 9k show the color coded results of the reconstruction as deformation analysis and kinematic analysis.

Figure 9D:
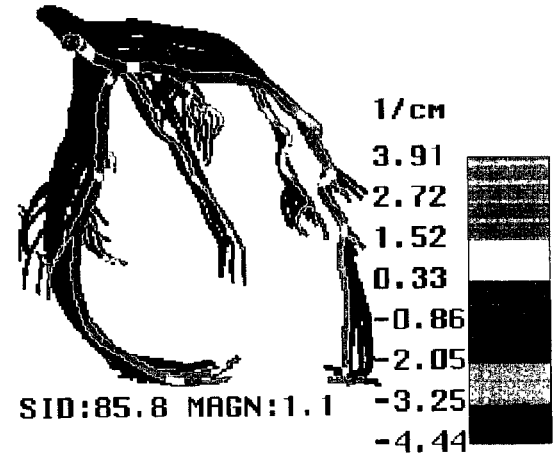
Figure 9E:
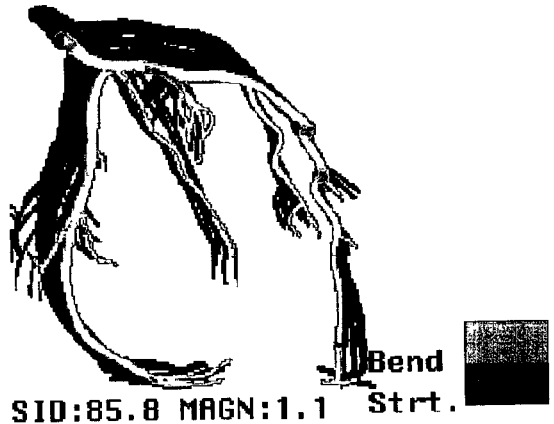

The reconstructed 3-D moving coronary arterial trees with the kinematic analyses throughout the cardiac cycle are illustrated in FIGS. 9c, 9d and 9e. In particular, FIG. 9c indicates the degree of curvature of the arterial tree over its range of motion through the cardiac cycle. six images are shown superimposed over one another corresponding to the six images in the original cine angiogram sequences. For clarity of this presentation, only one of the six 3D, color coded images is shown atop the others with others shown "greyed" out as "shadow" 3D images behind the top most image. In practice, the sequence of images may preferably be presented to the user as a sequence of 3D reconstructed images, each color coded to express a particular quantitative measure (if selected), such that the user may view the structure as a moving 3D model of the dynamic vascular structure. In one aspect of the invention, the user may interact with the system to select a particular "frame" of the 3D reconstructed views or may sequence through the frames in fast or slow motion to view the overall motion of the vascular structure. In all cases, a user may also request the quantitative analysis of a selected attribute so as to present the 3D model with color coding to represent the dynamic measure of the selected attribute through the cycle of motion of the vascular tree.

Figure 9F:
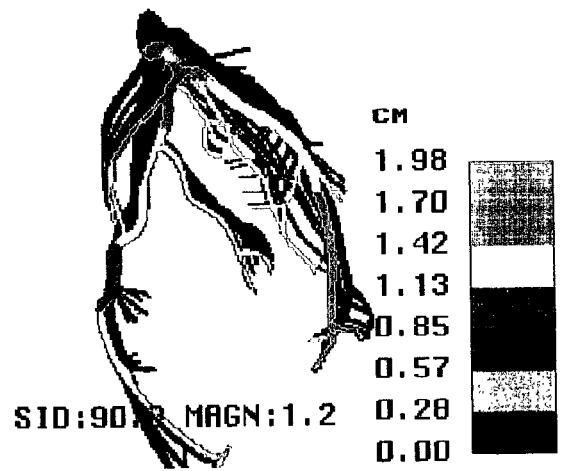

The deformation analyses in terms of curvature, torsion, and are illustrated in FIGS. 9f, 9g and 9h. The components of displacement, velocity, and acceleration along x-, y-, and z-axis are demonstrated in FIGS. 9i, 9j and 9k, respectively.

Figure 10C:
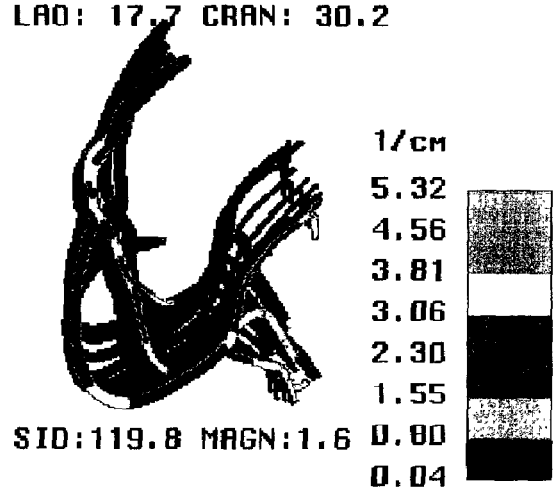
Figure 10D:
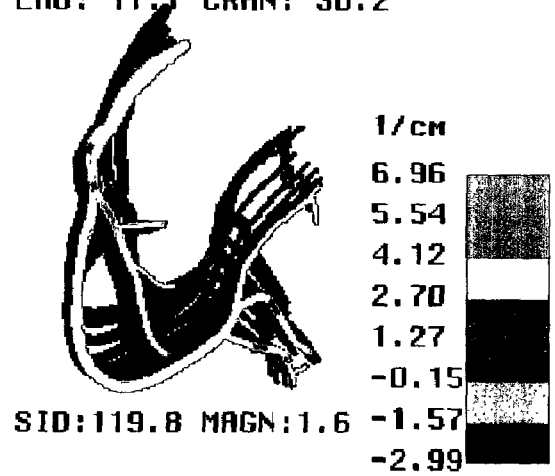
Figure 10E:
Figure 10F:
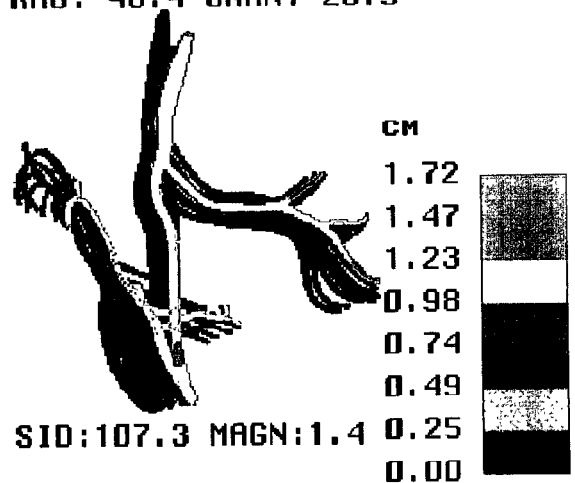
Figure 10G:
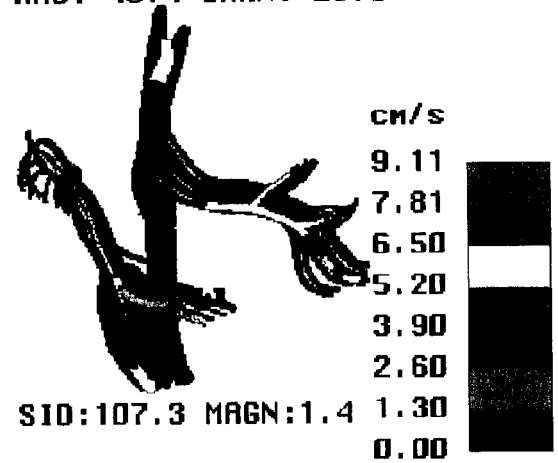
Figure 10H:
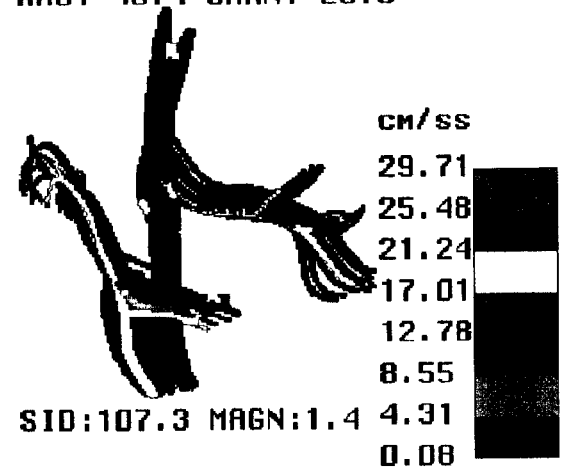

Similarly, another example is shown of right coronary cine angiograms acquired between end-diastole and end-systole, also from a single-plane imaging, in FIGS. 10a and 10b. The reconstructed dynamic 3-D coronary arterial trees with the corresponding kinematic and deformation analyses are shown in FIGS. 10c, 10d and 10e and FIGS. 10f, 10g and 10h. The components of displacement, velocity, and acceleration along x-axis, y-axis, and z-axis are shown in FIGS. 10i, 10j and 10k, respectively.

Figure 11:
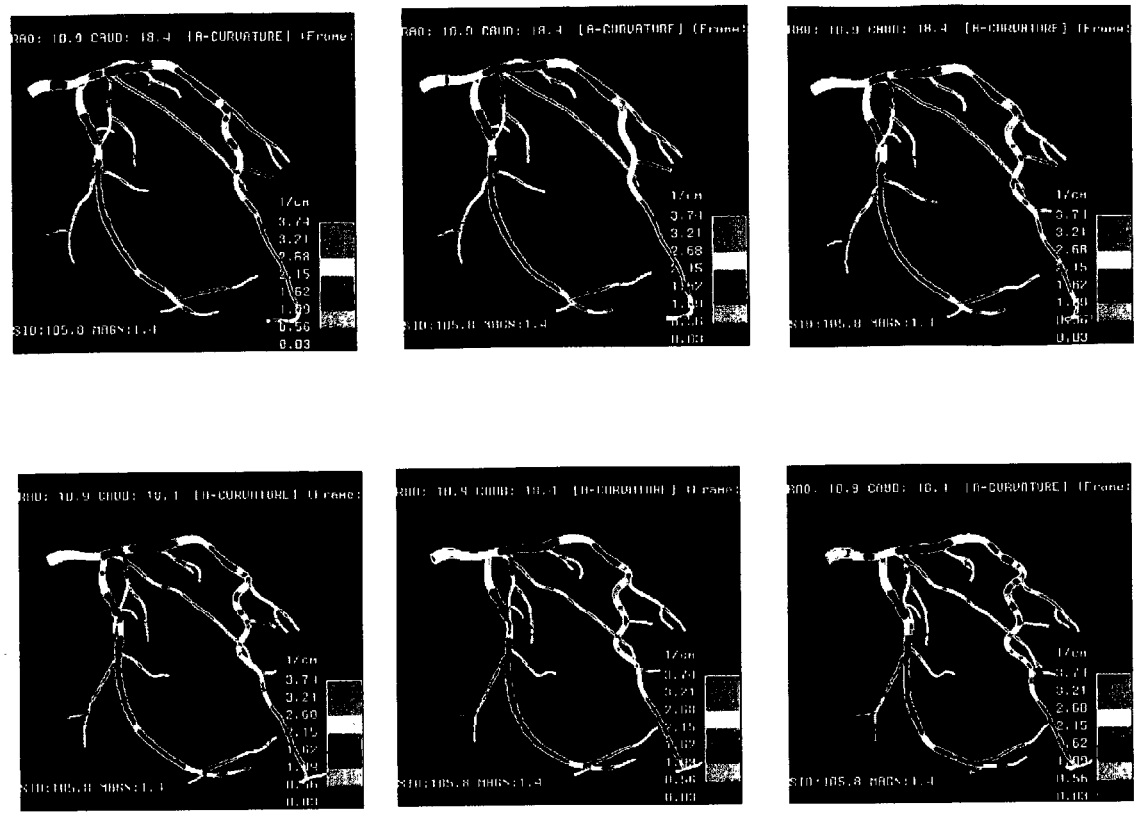
FIG. 11 is a sequence of exemplary, color-coded, curvature analysis displays corresponding to a first selected view of a reconstructed 3-D arterial tree.
Figure 12:
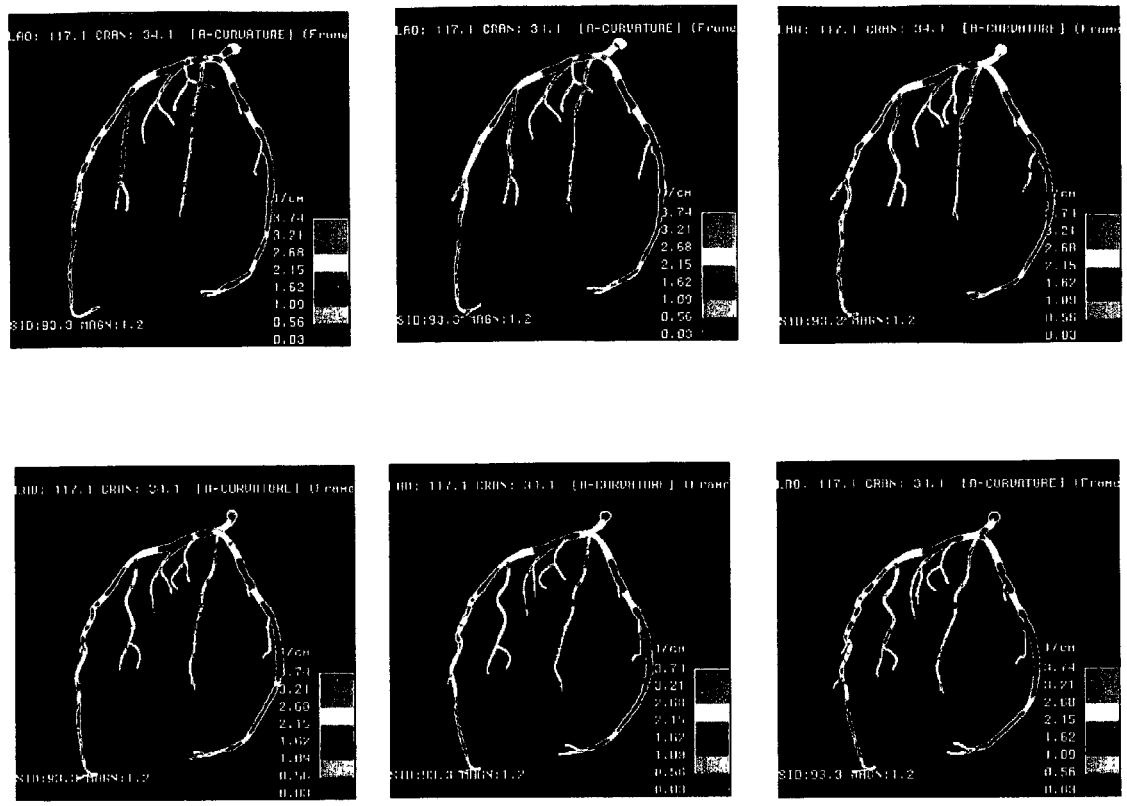
FIG. 12 is a sequence of exemplary, color-coded, curvature analysis displays corresponding to a second selected view of a reconstructed 3-D arterial tree.

FIGS. 9c–9k and 10c–10k show a sequence of time varying, color-coded displays indicating the value of a dynamic measure by the color coding at the corresponding section of the reconstructed 3-D arterial display. As noted above, the depiction of the time varying sequences of FIGS. 9c–9k and 10c–10k show the sequences of images overlaying one another on each figure with the last color-coded image of the sequence depicted on top. Earlier images in the sequence are shown "greyed" or "shadowed." FIG. 11 shows a similar sequence of color-coded 3-D arterial reconstructions as a sequence of 6 individual frames rather than overlayed as shown in FIGS. 9c–9k and 10c–10k. The sequence of displays in FIG. 11 represent an exemplary arterial tree display color-coded for curvature through the six frame sequence. FIG. 12 shows a similar sequence of images color-coded for curvature measures but viewed from an alternate selected viewing angle.

While the invention has been illustrated and described in the drawings and foregoing description, such illustration and description is to be considered as exemplary and not restrictive in character, it being understood that only the preferred embodiment and minor variants thereof have been shown and described and that all changes and modifications that come within the spirit of the invention are desired to be protected. In particular, those of ordinary skill in the art will recognize that the features of the invention to reconstruct a 3-D representation of cine-angiographic images (or cine images of other arterial tree structures) may be implemented as an appropriately programmed general or special purpose computer, as computational and imaging electronics and devices as may be commercially available or as custom computational and imaging devices and electronics, or as combinations of such software, firmware and hardware components. Such design choices among such a variety of means are well known to those of ordinary skill in the art.

What is claimed is:

1. A method for analysis of dynamic arterial tree structures comprising the steps of:
   providing a time varying 3D representation of a moving arterial tree structure; and
   displaying analysis of said time varying 3D representation in response to interactive user input,
   wherein the step of providing a 3D representation includes the steps of:
   providing a first sequence of time varying 2D arteriograms derived from a first angular view;
   providing a second sequence of time varying 2D arteriograms derived from a second angular view;
   reconstructing said time varying 3D representation of said moving arterial tree structure using said first sequence and using said second sequence; and
   establishing temporal correspondence of points in said time varying 3D representation the temporal correspondence being computed in accordance with Hamilton's Principle.

2. The method of claim 1 wherein the step of establishing comprises the step of:
   providing smoothness constraints,
   wherein the step of establishing temporal correspondence of points in said time varying 3D representation computes the temporal correspondence in accordance with Hamilton's Principle and using said smoothness constraints.

3. The method of claim 1 wherein the step of displaying analysis comprises the steps of:
   determining a magnitude of displacement for a selected segment of said time varying 3D representation using the temporal correspondence; and
   displaying said magnitude of displacement on a user display.

4. The method of claim 3 wherein the step of displaying said magnitude of displacement comprises the step of:
   displaying said magnitude of displacement as color coded magnitudes of displacement at each of a plurality of points along said selected segment.

5. The method of claim 1 wherein the step of displaying analysis comprises the steps of:
   determining a velocity for a selected segment of said time varying 3D representation using the temporal correspondence; and
   displaying said velocity on a user display.

6. The method of claim 5 wherein the step of displaying said velocity comprises the step of:
   displaying said velocity as color coded velocity at each of a plurality of points along said selected segment.

7. The method of claim 1 wherein the step of displaying analysis comprises the steps of:
   determining an acceleration for a selected segment of said time varying 3D representation using the temporal correspondence; and
   displaying said acceleration on a user display.

8. The method of claim 7 wherein the step of displaying said acceleration comprises the step of:
   displaying said acceleration as color coded acceleration at each of a plurality of points along said selected segment.

9. The method of claim 1 wherein the step of displaying analysis comprises the steps of:
   determining a curvature for a selected segment of said time varying 3D representation using the temporal correspondence; and
   displaying said curvature on a user display.

10. The method of claim 9 wherein the step of displaying said curvature comprises the step of:
    displaying said curvature as color coded curvature at each of a plurality of points along said selected segment.

11. The method of claim 1 wherein the step of displaying analysis comprises the steps of:
    determining a tortuosity for a selected segment of said time varying 3D representation using the temporal correspondence; and
    displaying said tortuosity on a user display.

12. The method of claim 11 wherein the step of displaying said tortuosity comprises the step of:
    displaying said tortuosity as color coded tortuosity at each of a plurality of points along said selected segment.

13. The method of claim 1 wherein the step of displaying analysis comprises the steps of:
    determining a flexion angle for a selected segment of said time varying 3D representation using the temporal correspondence; and
    displaying said flexion angle on a user display.

14. The method of claim 13 wherein the step of displaying said flexion angle comprises the step of:
    displaying said flexion angle as color coded flexion measure at each of a plurality of points along said selected segment.

15. The method of claim 13 wherein the step of determining a flexion angle includes the step of:
    determining a flexion point as one of a plurality of points along said selected segment.

16. The method of claim 15 wherein the step of determining a flexion point comprises the step of:
    determining said flexion point as a point having a local maximum flexion angle as compared to all other points of said plurality of points along said selected segment.

17. The method of claim 15 wherein the step of determining a flexion point comprises the step of:
    determining said flexion point as a point having a local minimum flexion angle as compared to all other points of said plurality of points along said selected segment.

18. A system for analysis of dynamic arterial trees comprising:
    means for providing a time varying 3D representation of a moving arterial tree structure; and
    means for displaying analysis of said time varying 3D representation in response to interactive user input,
    wherein the means for providing includes:
    means for providing a first sequence of time varying 2D arteriograms derived from a first angular view;
    means for providing a second sequence of time varying 2D arteriograms derived from a second angular view;
    means for reconstructing said time varying 3D representation using said first sequence and using said second sequence; and
    means for establishing temporal correspondence of points in said time varying 3D representation the temporal correspondence being computed in accordance with Hamilton's Principle.

19. The system of claim 18 wherein the means for establishing comprises:
    means for providing smoothness constraints,
    wherein the means for establishing temporal correspondence is operable in accordance with Hamilton's Principle and is operable using said smoothness constraints.

20. The system of claim 18 wherein the means for displaying analysis comprises:

means for determining a magnitude of displacement for a selected segment of said time varying 3D representation using the temporal correspondence; and means for displaying said magnitude of displacement on a user display.

21. The system of claim 20 wherein the means for displaying said magnitude of displacement comprises:

means for displaying said magnitude of displacement as color coded magnitudes of displacement at each of a plurality of points along said selected segment.

22. The system of claim 18 wherein the means for displaying analysis comprises:

means for determining a velocity for a selected segment of said time varying 3D representation using the temporal correspondence; and means for displaying said velocity on a user display.

23. The system of claim 22 wherein the means for displaying said velocity comprises:

means for displaying said velocity as color coded velocity at each of a plurality of points along said selected segment.

24. The system of claim 18 wherein the means for displaying analysis comprises:

means for determining an acceleration for a selected segment of said time varying 3D representation using the temporal correspondence; and means for displaying said acceleration on a user display.

25. The system of claim 24 wherein the means for displaying said acceleration comprises:

means for displaying said acceleration as color coded acceleration at each of a plurality of points along said selected segment.

26. The system of claim 18 wherein the means for displaying analysis comprises:

means for determining a curvature for a selected segment of said time varying 3D representation using the temporal correspondence; and means for displaying said curvature on a user display.

27. The system of claim 26 wherein the means for displaying said curvature comprises:

means for displaying said curvature as color coded curvature at each of a plurality of points along said selected segment.

28. The system of claim 18 wherein the means for displaying analysis comprises:

means for determining a tortuosity for a selected segment of said time varying 3D representation using the temporal correspondence; and means for displaying said tortuosity on a user display.

29. The system of claim 28 wherein the means for displaying said tortuosity comprises:

means for displaying said tortuosity as color coded tortuosity at each of a plurality of points along said selected segment.

30. The system of claim 18 wherein the means for displaying analysis comprises:

means for determining a flexion angle for a selected segment of said time varying 3D representation using the temporal correspondence; and means for displaying said flexion angle on a user display.

31. The system of claim 30 wherein the means for displaying said flexion angle comprises:

means for displaying said flexion angle as color coded flexion measure at each of a plurality of points along said selected segment.

32. The system of claim 30 wherein the means for determining a flexion angle includes:

means for determining a flexion point as one of a plurality of points along said selected segment.

33. The system of claim 32 wherein the means for determining a flexion point comprises:

means for determining said flexion point as a point having a local maximum flexion angle as compared to all other points of said plurality of points along said selected segment.

34. The system of claim 32 wherein the means for determining a flexion point comprises:

means for determining said flexion point as a point having a local minimum flexion angle as compared to all other points of said plurality of points along said selected segment.

* * * * *